(12) United States Patent
Craig et al.

(10) Patent No.: US 11,617,599 B2
(45) Date of Patent: Apr. 4, 2023

(54) ULTRASONIC SURGICAL INSTRUMENT

(71) Applicant: Covidien LP, Mansfield, MA (US)

(72) Inventors: Jason L. Craig, Loveland, CO (US); Kenneth E. Netzel, Loveland, CO (US); Michael J. Brown, Superior, CO (US); Christopher T. Tschudy, Arvada, CO (US); Weng-Kai Lee, Longmont, CO (US)

(73) Assignee: Covidien LP, Mansfield, MA (US)

( * ) Notice: Subject to any disclaimer, the term of this patent is extended or adjusted under 35 U.S.C. 154(b) by 106 days.

(21) Appl. No.: 17/071,263

(22) Filed: Oct. 15, 2020

(65) Prior Publication Data
US 2022/0117622 A1    Apr. 21, 2022

(51) Int. Cl.
*A61B 17/32* (2006.01)
*A61B 17/00* (2006.01)

(52) U.S. Cl.
CPC ........ *A61B 17/320092* (2013.01); *A61B 17/00234* (2013.01); *A61B 2017/00526* (2013.01); *A61B 2017/00734* (2013.01); *A61B 2017/320074* (2017.08); *A61B 2017/320094* (2017.08)

(58) Field of Classification Search
CPC ........ A61B 17/2909; A61B 17/320092; A61B 2017/00353; A61B 2017/00424; A61B 2017/2825; A61B 2017/2911; A61B 2017/320094; A61B 2017/320095; A61B 2017/2845; A61B 17/00234; A61B 2017/0046; A61B 2017/00526; A61B 2017/00734; A61B 2017/2929; A61B 2017/2932; A61B 2017/320074; A61B 2090/032; A61B 2090/065
See application file for complete search history.

(56) References Cited

U.S. PATENT DOCUMENTS

| | | |
|---|---|---|
| 1,813,902 A | 7/1931 | Bovie |
| 2,235,274 A | 3/1941 | Trehern |
| 2,874,470 A | 2/1959 | Richards |
| 2,990,616 A | 7/1961 | Balamuth |
| 3,432,691 A | 3/1969 | Shoh |
| 3,489,930 A | 1/1970 | Shoh |
| 3,526,792 A | 9/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |

(Continued)

*Primary Examiner* — Mohamed G Gabr
(74) *Attorney, Agent, or Firm* — Carter, DeLuca & Farrell LLP

(57) ABSTRACT

A surgical instrument includes a housing, an end effector including a clamp jaw, a drive member extending distally from the housing, and a clamp lever pivotably coupled to the housing. The drive member is operably coupled to the clamp jaw such that translation of the drive member pivots the clamp jaw from an open position towards a clamping position. The clamp lever is operably coupled to the drive member via a rigid slider. The clamp jaw is configured to provide a jaw force to clamped tissue, measured at about 0.192 inches from a distal end of the clamp jaw, of from about 1 lbf to about 8 lbf in response to a full actuation of the clamp lever.

18 Claims, 15 Drawing Sheets

(56) References Cited

U.S. PATENT DOCUMENTS

| | | |
|---|---|---|
| 4,227,110 A | 10/1980 | Douglas et al. |
| 4,300,083 A | 11/1981 | Heiges |
| 4,302,728 A | 11/1981 | Nakamura |
| 4,370,302 A | 1/1983 | Suzuoka et al. |
| 4,641,053 A | 2/1987 | Takeda |
| 5,113,116 A | 5/1992 | Wilson |
| 5,224,680 A | 7/1993 | Greenstein et al. |
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,565,520 A | 10/1996 | Fock et al. |
| 5,582,617 A | 12/1996 | Klieman et al. |
| 5,593,414 A | 1/1997 | Shipp et al. |
| 5,685,311 A | 11/1997 | Hara |
| 5,717,306 A | 2/1998 | Shipp |
| 5,728,130 A | 3/1998 | Ishikawa et al. |
| 5,776,155 A | 7/1998 | Beaupre et al. |
| 5,792,138 A | 8/1998 | Shipp |
| 5,796,056 A | 8/1998 | Bredow et al. |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,162,194 A | 12/2000 | Shipp |
| 6,183,426 B1 | 2/2001 | Akisada et al. |
| 6,220,098 B1 | 4/2001 | Johnson et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,977,587 B2 | 7/2011 | Rajagopal et al. |
| 8,435,258 B2 | 5/2013 | Young et al. |
| 8,672,959 B2 | 3/2014 | Witt et al. |
| 8,974,447 B2 | 3/2015 | Kimball et al. |
| 9,943,325 B2 | 4/2018 | Faller et al. |
| 10,010,341 B2 | 7/2018 | Houser et al. |
| 10,368,898 B2 | 8/2019 | Brown et al. |
| 10,874,418 B2 | 12/2020 | Houser et al. |
| 2001/0048855 A1 | 12/2001 | Lin |
| 2002/0002379 A1 | 1/2002 | Bishop |
| 2002/0077645 A1 | 6/2002 | Wiener et al. |
| 2002/0091339 A1 | 7/2002 | Horzewski et al. |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0256487 A1 | 12/2004 | Collins et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0079875 A1* | 4/2006 | Faller ............ A61B 17/320092 606/40 |
| 2006/0079878 A1 | 4/2006 | Houser |
| 2006/0079879 A1 | 4/2006 | Faller et al. |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0149881 A1 | 6/2007 | Rabin |
| 2007/0166663 A1 | 7/2007 | Telles et al. |
| 2007/0175960 A1 | 8/2007 | Shelton et al. |

(56) References Cited

U.S. PATENT DOCUMENTS

| | | |
|---|---|---|
| 2007/0227866 A1 | 10/2007 | Dimig |
| 2007/0239028 A1 | 10/2007 | Houser et al. |
| 2007/0239101 A1 | 10/2007 | Kellogg |
| 2007/0282333 A1 | 12/2007 | Fortson et al. |
| 2008/0033248 A1 | 2/2008 | Akagi |
| 2008/0051693 A1 | 2/2008 | Babaev |
| 2008/0245841 A1 | 10/2008 | Smith et al. |
| 2009/0138006 A1 | 5/2009 | Bales et al. |
| 2009/0143797 A1 | 6/2009 | Smith et al. |
| 2009/0143805 A1 | 6/2009 | Palmer et al. |
| 2009/0223033 A1 | 9/2009 | Houser |
| 2010/0004669 A1 | 1/2010 | Smith et al. |
| 2010/0090420 A1 | 4/2010 | Nickels, Jr. et al. |
| 2011/0024145 A1* | 2/2011 | Click ................. A61B 17/8827 173/2 |
| 2012/0078278 A1 | 3/2012 | Bales, Jr. et al. |
| 2013/0338691 A1 | 12/2013 | Young et al. |
| 2014/0107684 A1 | 4/2014 | Craig |
| 2015/0148830 A1 | 5/2015 | Stulen et al. |
| 2015/0245850 A1 | 9/2015 | Hibner et al. |

\* cited by examiner

ULTRASONIC SURGICAL INSTRUMENT

BACKGROUND

Technical Field

The present disclosure relates to surgical instruments and, more particularly, to an ultrasonic surgical instrument configured to treat tissue with ultrasonic energy.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue.

Typically, an ultrasonic surgical instrument is configured to transmit ultrasonic energy produced by a generator and transducer assembly along a waveguide to an end effector that is spaced-apart from the generator and transducer assembly. With respect to cordless ultrasonic instruments, for example, a portable power source, e.g., a battery, and the generator and transducer assembly are mounted on the handheld instrument itself, while the waveguide interconnects the generator and transducer assembly with the end effector. Tethered ultrasonic instruments operate in similar fashion except that, rather than having the generator and power source mounted on the handheld instrument itself, the handheld instrument is configured to connect to a standalone power supply and/or generator via a corded connection.

SUMMARY

As used herein, the term "distal" refers to the portion that is being described which is further from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, and/or other variations, up to and including plus or minus 10 percent. Further, any or all of the aspects described herein, to the extent consistent, may be used in conjunction with any or all of the other aspects described herein.

Provided in accordance with aspects of the present disclosure is a surgical instrument including a housing, an end effector including a clamp jaw pivotable from an open position towards a clamping position, a drive member extending distally from the housing, and a clamp lever pivotably coupled to the housing. The drive member is operably coupled to the clamp jaw such that translation of the drive member pivots the clamp jaw from the open position towards the clamping position. The clamp lever is operably coupled to the drive member via a rigid slider. The clamp jaw is configured to provide a jaw force to tissue clamped between the clamp jaw and an opposing structure, measured at about 0.192 inches from a distal end of the clamp jaw, of from about 1 lbf to about 8 lbf in response to a full actuation of the clamp lever.

In an aspect of the present disclosure, a lever force, measured at a midpoint of the clamp lever, of from about 1 lbf to about 10 lbf is required to fully actuate the clamp lever.

In another aspect of the present disclosure, the surgical instrument further includes a waveguide extending distally from the housing and having a blade at a distal end thereof. The blade defines the opposing structure. The waveguide is configured to transmit ultrasonic energy to the blade. The clamp jaw is configured to oppose the blade in the clamping position thereof.

In another aspect of the present disclosure, an ultrasonic transducer is mounted on the housing and coupled to the waveguide. The ultrasonic transducer is configured to generate ultrasonic energy for transmission along the waveguide to the blade.

In yet another aspect of the present disclosure, the clamp lever is pivotably coupled to the housing on a first side of a longitudinal axis of the drive member, the clamp lever is actuatable via a grasping portion disposed on a second, opposite side of the longitudinal axis, and the rigid slider is substantially aligned on the longitudinal axis. In such aspects, actuation of the clamp lever may translate the rigid slider proximally to thereby move the drive member proximally to pivot the clamp jaw towards the clamping position. Additionally or alternatively, the clamp lever includes a proximal contact surface configured to urge the rigid slider proximally in response to actuation of the clamp lever.

In still another aspect of the present disclosure, a linkage is coupled between the rigid slider and the clamp lever. In such aspects, actuation of the clamp lever urges the linkage proximally to thereby urge the rigid slider proximally.

In still yet another aspect of the present disclosure, the full actuation of the clamp lever includes moving the clamp lever from an initial position to a hard stop. The hard stop may be defined by contact of a portion of the clamp lever with a portion of the housing.

Another surgical instrument provided in accordance with aspects of the present disclosure includes a housing, a waveguide extending distally from the housing and having a blade at a distal end thereof, drive and support members extending distally from the housing, a clamp jaw pivotably supported at a distal end portion of the support member and operably coupled to a distal end portion of the drive member such that translation of the drive member relative to the support member pivots the clamp jaw relative to the blade from an open position towards a clamping position, a clamp lever pivotably coupled to the housing, and a drive assembly. The clamp jaw includes a tissue-contacting surface configured to oppose the blade in the clamping position of the clamp jaw. The tissue-contacting surface defines a tissue-contacting surface area. The drive assembly includes a rigid slider operably coupling the clamp lever with the drive member. The clamp jaw, in response to a full actuation of the clamp lever, imparts an average jaw pressure of from about 35 psi to about 285 psi to tissue clamped between the tissue-contacting surface of the clamp jaw and the blade.

In an aspect of the present disclosure, a lever force, measured at a midpoint of the clamp lever, of from about 1 lbf to about 10 lbf is required to fully actuate the clamp lever.

In another aspect of the present disclosure, the surgical instrument further includes an ultrasonic transducer mounted on the housing, coupled to the waveguide, and configured to generate ultrasonic energy for transmission along the waveguide to the blade.

In still another aspect of the present disclosure, the clamp lever is pivotably coupled to the housing on a first side of a longitudinal axis of the drive member, the clamp lever is actuatable via a grasping portion disposed on a second, opposite side of the longitudinal axis, and the rigid slider is substantially aligned on the longitudinal axis. In such aspects, actuation of the clamp lever may translate the rigid slider proximally to thereby move the drive member proximally to pivot the clamp jaw towards the clamping position. Alternatively or additionally, the clamp lever includes a proximal contact surface configured to urge the rigid slider proximally in response to actuation of the clamp lever.

In yet another aspect of the present disclosure, a linkage is coupled between the rigid slider and the clamp lever. Actuation of the clamp lever urges the linkage proximally to thereby urge the rigid slider proximally.

In still yet another aspect of the present disclosure, the full actuation of the clamp lever includes moving the clamp lever from an initial position to a hard stop. The hard stop may be defined by contact of a portion of the clamp lever with a portion of the housing.

In another aspect of the present disclosure, the clamp lever is pivotably coupled to the housing on a first side of a longitudinal axis of the drive member, the clamp lever is actuatable via a grasping portion disposed on the first side of the longitudinal axis, and the rigid slider is substantially aligned on the longitudinal axis.

An ultrasonic surgical instrument provided in accordance with aspects of the present disclosure includes a housing, a waveguide extending distally from the housing and having a blade at a distal end thereof, an end effector including the blade and a clamp jaw, a drive member extending from the housing to the end effector and operably coupled to the clamp jaw, a rigid slider operably coupled to a proximal end portion of the drive member, and a clamp lever having an initial position and an actuated position. The waveguide is configured to transmit ultrasonic energy to the blade. The clamp jaw is pivotable relative to the blade from an open position towards a clamping position to clamp tissue therebetween. Translation of the drive member pivots the clamp jaw from the open position towards the clamping position to exert a jaw force on the clamped tissue. Translation of the rigid slider results in corresponding translation of the drive member. The clamp lever is actuatably coupled to the housing and operably coupled to the rigid slider such that a full actuation of the clamp lever from the initial position to the actuated position translates the rigid slider and the drive member to thereby pivot the clamp jaw from the open position towards the clamping position with substantially no dampening of the jaw force.

In an aspect of the present disclosure, an ultrasonic transducer is mounted on the housing and coupled to the waveguide to generate ultrasonic energy for transmission along the waveguide to the blade.

In another aspect of the present disclosure, the clamp lever is pivotably coupled to the housing on a first side of a longitudinal axis of the drive member, the clamp lever is actuatable via a grasping portion disposed on a second, opposite side of the longitudinal axis, and the rigid slider is substantially aligned on the longitudinal axis.

In another aspect of the present disclosure, actuation of the clamp lever translates the rigid slider proximally to thereby move the drive member proximally to pivot the clamp jaw towards the clamping position.

In yet another aspect of the present disclosure, the clamp lever includes a proximal contact surface configured to urge the rigid slider proximally in response to actuation of the clamp lever.

In still another aspect of the present disclosure, a linkage is coupled between the rigid slider and the clamp lever. In such aspects, actuation of the clamp lever urges the linkage proximally to thereby urge the rigid slider proximally.

In still yet another aspect of the present disclosure, a hard stop is defined at the actuated position of the clamp lever. The hard stop may be defined by contact of a portion of the clamp lever with a portion of the housing.

In another aspect of the present disclosure, the rigid slider includes an inner retainer longitudinally fixed relative to the proximal end portion of the drive member and an outer slider slidably disposed about the inner retainer. In such aspects, actuation of the clamp lever urges the outer slider to translate, thereby correspondingly translating the inner retainer and, in turn, correspondingly translating the drive member.

In yet another aspect of the present disclosure, the rigid slider is rotatable relative to the drive member.

In still another aspect of the present disclosure, the inner retainer is rotationally fixed relative to the drive member and the outer slider is rotatable relative to the inner retainer and the drive member.

A method of manufacturing an ultrasonic surgical instrument in accordance with aspects of the present disclosure includes assembling an ultrasonic surgical instrument to include a clamp lever operably coupled to a clamp jaw via a rigid slider and a drive member such that actuation of the clamp lever translates the rigid slider and the drive member together to thereby pivot the clamp jaw, measuring a lever force required to fully actuate the clamp lever, determining whether the measured lever force is within a lever force setting range, measuring a jaw force applied by the clamp jaw in response to full actuation of the clamp lever, and determining whether the measured jaw force is within a jaw force setting range.

In an aspect of the present disclosure, the lever force is measured at a midpoint of the clamp lever and the lever force setting range is from about 1 lbf to about 10 lbf.

In another aspect of the present disclosure, the jaw force is measured at about 0.192 inches from a distal end of the jaw member and the jaw force setting range is from about 1 lbf to about 8 lbf.

In yet another aspect of the present disclosure, in a case where the measured lever force is within the lever force setting range and the measured jaw force is within the jaw force setting range, the method further includes accepting the ultrasonic surgical instrument.

In still another aspect of the present disclosure, in a case where the measured lever force is outside of the lever force setting range or the measured jaw force is outside of the jaw force setting range, the method further includes rejecting the ultrasonic surgical instrument.

In still yet another aspect of the present disclosure, measuring the jaw force includes positioning the ultrasonic surgical instrument in a first testing assembly and actuating the clamp lever to clamp the clamp jaw against a sensor of the first testing assembly to measure the force applied by the clamp jaw.

In another aspect of the present disclosure, measuring the lever force includes positioning the ultrasonic surgical instrument in a second testing assembly, fully actuating the clamp lever using the second testing assembly, and measuring a force applied by the second testing assembly to fully actuate the clamp lever.

In still another aspect of the present disclosure, assembling the ultrasonic surgical instrument further includes engaging a contact surface of the clamp lever with a contact surface of the rigid slider such that actuation of the clamp lever translates the rigid slider.

In yet another aspect of the present disclosure, assembling the ultrasonic surgical instrument further includes coupling a linkage between the clamp lever and the rigid slider such that actuation of the clamp lever translates the linkage to thereby translate the rigid slider.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
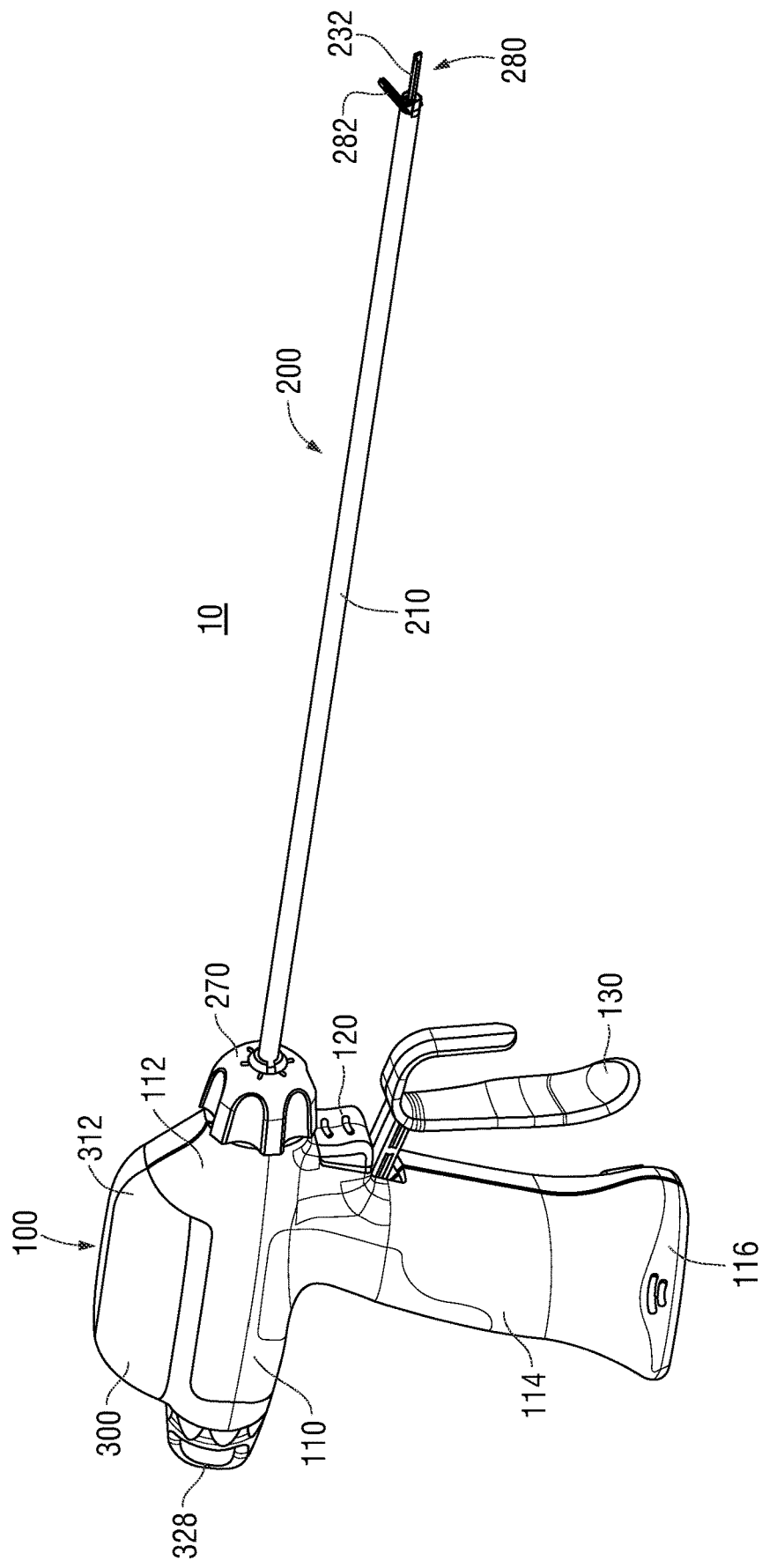
FIG. 1 is a perspective view of an ultrasonic surgical instrument provided in accordance with the present disclosure.
Figure 2:
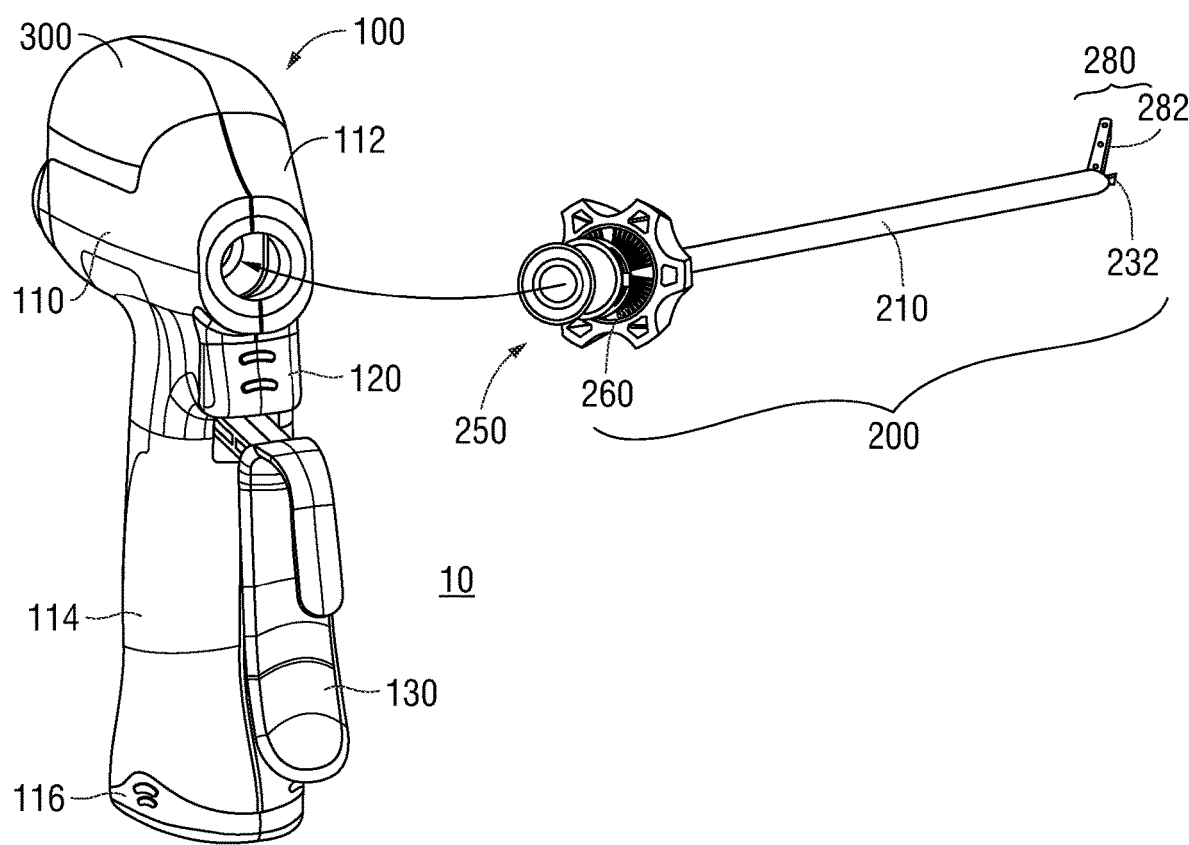
FIG. 2 is a perspective view of the ultrasonic surgical instrument of FIG. 1 with a handle assembly of the ultrasonic instrument separated from an elongated assembly of the ultrasonic surgical instrument.
Figure 3:
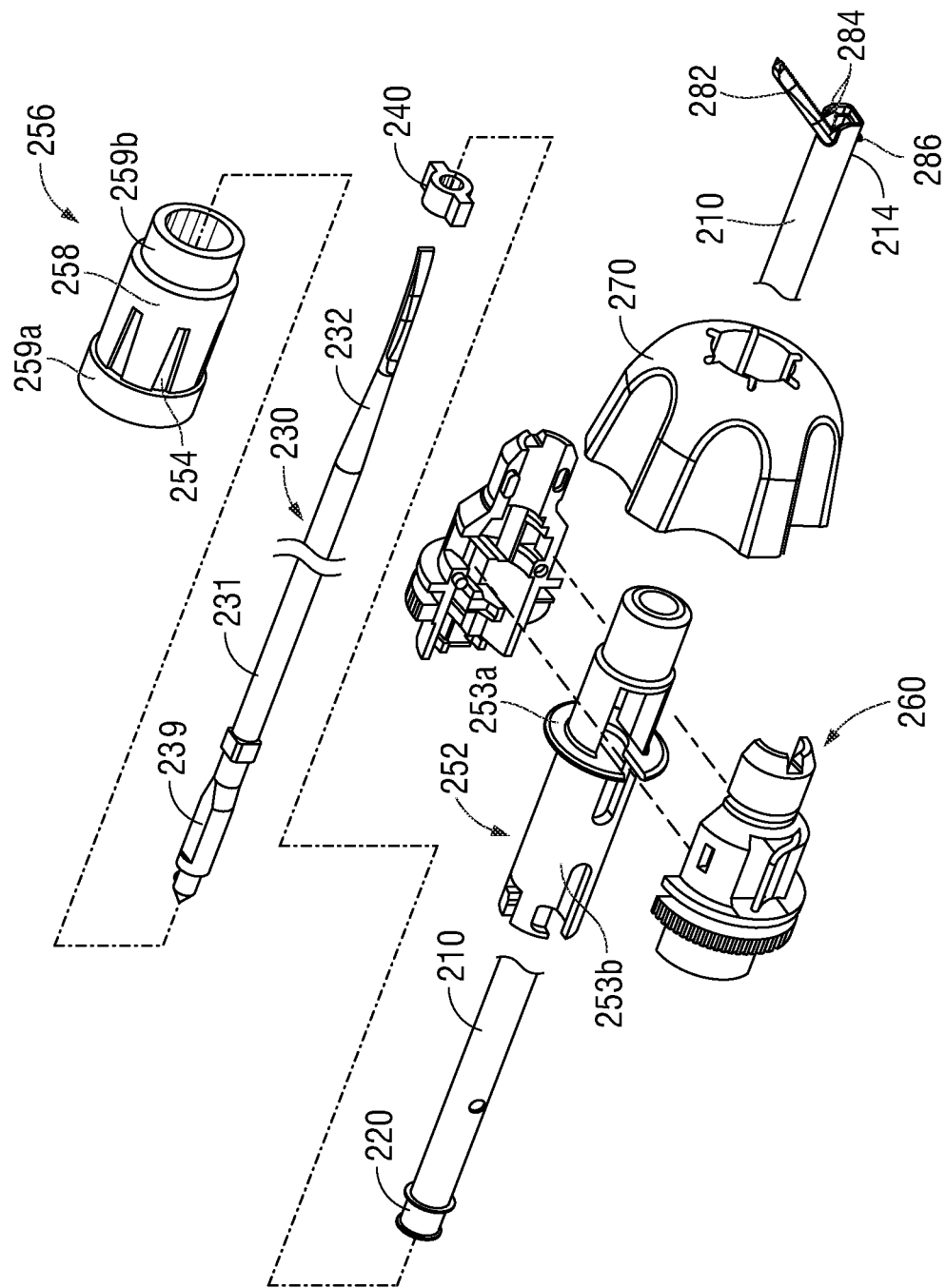
FIG. 3 is an exploded, perspective view of the elongated assembly of the ultrasonic surgical instrument of FIG. 1.

Referring generally to FIGS. 1-5, an ultrasonic surgical instrument provided in accordance with the aspects and features of the present disclosure is shown generally identified by reference numeral 10. Ultrasonic surgical instrument 10 generally includes a handle assembly 100 and an elongated assembly 200 engaged with handle assembly 100. Handle assembly 100 includes a housing 110 defining a body portion 112 configured to support an ultrasonic transducer and generator assembly ("TAG") 300, and a fixed handle portion 114 defining a compartment 116 configured to receive a battery assembly 400. Handle assembly 100 further includes an activation button 120 operably positioned to electrically couple between TAG 300 and battery assembly 400 when TAG 300 is mounted on body portion 112 of housing 110 and battery assembly 400 is engaged within compartment 116 of housing 110.

A clamp lever 130 extends from housing 110 of handle assembly 100 adjacent fixed handle portion 114 of housing 110. Clamp lever 130 includes a grasping portion 131 extending from body portion 112 of housing 110, a bifurcated drive portion 132 extending into body portion 112 of housing 110, and a connector portion 133 interconnecting grasping portion 131 and bifurcated drive portion 132. Bifurcated drive portion 132 is selectively movable relative to housing 110 to actuate ultrasonic surgical instrument 10, as detailed below. Bifurcated drive portion 132 of clamp lever 130 is pivotably connected to body portion 112 of housing 110 about a pivot axis 134 via one or more pivotable engagements, e.g., pivot bosses and corresponding recesses, a pivot pin, etc. Bifurcated drive portion 132 further includes a proximal contact surface 136 and a distal contact surface 138. Proximal and distal contact surfaces 136, 138 may be similarly configured or differently configured and may define linear configuration, angled configurations, curved configurations, protruding portion(s), recessed portion(s), or any other suitable configuration. Connector portion 133 of clamp lever 130 interfaces with a return spring 139a disposed about a return spring shaft 139b. Return spring 139a biases connector portion 133 of clamp lever 130 distally and, thus, biases clamp lever 130 towards an initial or un-actuated position, wherein clamp lever 130 is distally spaced-apart from fixed handle portion 114 of housing 110.

TAG 300 and battery assembly 400 are each removable from handle assembly 100 to facilitate disposal of handle assembly 100 after a single use or to enable sterilization of handle assembly 100 for subsequent use. TAG 300 may be configured to withstand sterilization such that TAG 300 may be sterilized for repeated use. Battery assembly 400, on the other hand, is configured to be aseptically transferred and retained within compartment 116 of fixed handle portion 114 of housing 110 of handle assembly 100 such that battery assembly 400 may be repeatedly used without requiring sterilization thereof, although other configurations are also contemplated. As an alternative to the cordless, battery-powered configuration shown and described herein, ultrasonic surgical instrument 10 may be configured as a tethered device wherein the generator and power source are remotely disposed and connected to the transducer (which is supported on body portion 112 of housing 110) by way of a cable.

An electrical connector 140 disposed within housing 110 of handle assembly 100 includes TAG contacts 142, battery assembly contacts 144, and an activation button connector 146. Electrical connector 140 electrically couples to activation button 120 via activation button connector 146, is configured to electrically couple to TAG 300 via TAG contacts 142 upon engagement of TAG 300 with body portion 112 of housing 110 of handle assembly 100, and is configured to electrically couple to battery assembly 400 via battery assembly contacts 144 upon engagement of battery assembly 400 within compartment 116 of fixed handle portion 114 of housing 110 of handle assembly 100. As such, in use, when activation button 120 is activated in an appropriate manner, an underlying two-mode switch assembly 122 is activated to supply power from battery assembly 400 to TAG 300 in either a "LOW" power mode or a "HIGH" power mode, depending upon the manner of activation of activation button 120. However, other suitable activation configurations employing different and/or multiple buttons, switches, modes, etc., are also contemplated.

Figure 4:
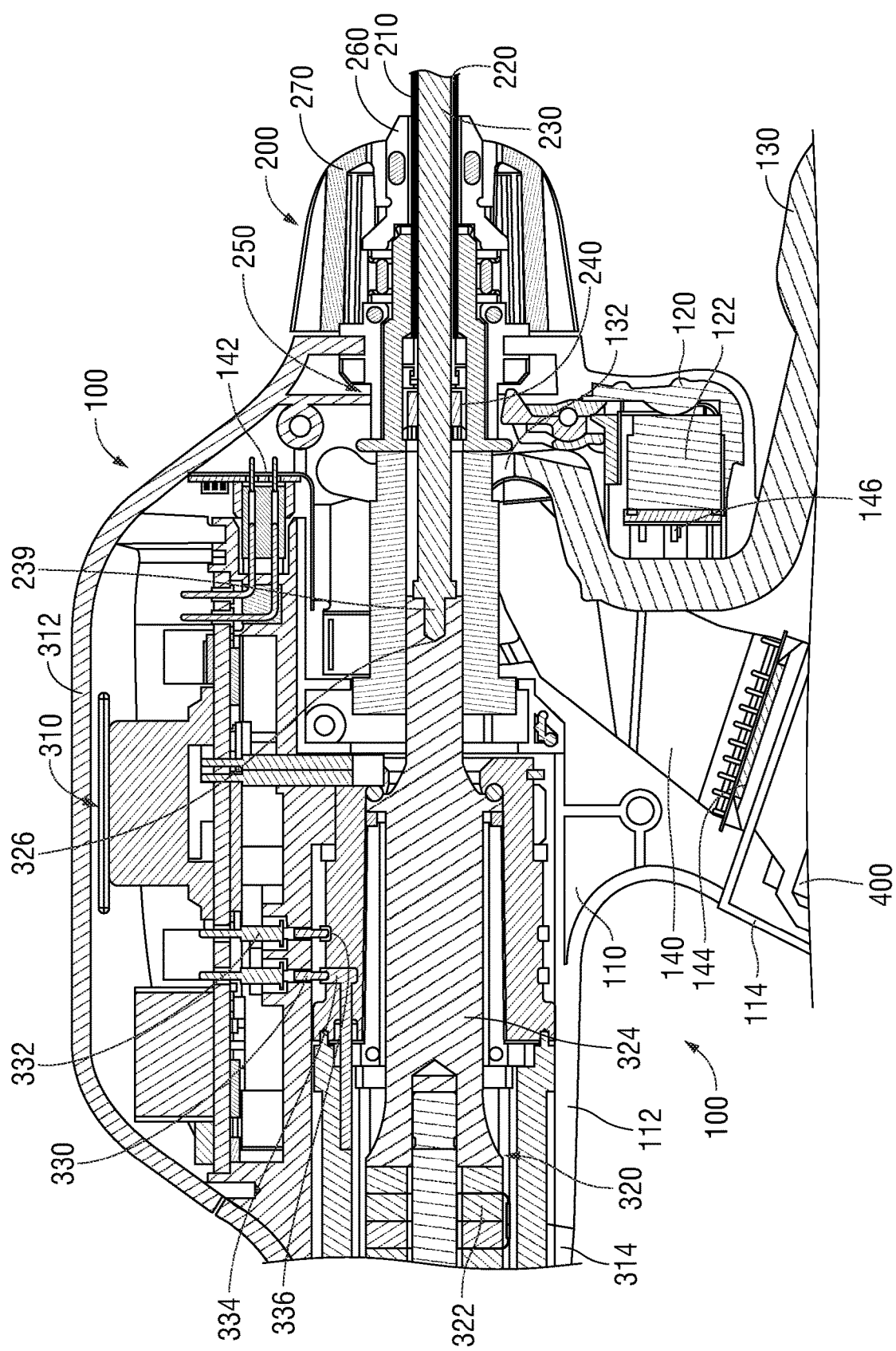
FIG. 4 is an enlarged, longitudinal, cross-sectional view of a proximal portion of the ultrasonic surgical instrument of FIG. 1.

With particular reference to FIG. 4, TAG 300 includes a generator 310 and an ultrasonic transducer 320. Generator 310 includes a housing 312 configured to house the internal electronics of generator 310, and a cradle 314 configured to rotatably support ultrasonic transducer 320. Ultrasonic transducer 320 includes a piezoelectric stack 322 and a distally-extending horn 324. Horn 324 defines a female receiver 326, e.g., defining internal threading, at the free distal end thereof. A set of connectors 330, 332 and corresponding rotational contacts 334, 336 associated with generator 310 and ultrasonic transducer 320, respectively, enable drive signals to be communicated from generator 310 to piezoelectric stack 322 to drive ultrasonic transducer 320. More specifically, piezoelectric stack 322 of ultrasonic transducer 320 converts a high voltage AC signal received from generator 310 into mechanical motion that is output from horn 324 to elongated assembly 200. Ultrasonic transducer 320 further includes a rotation knob 328 (FIG. 1) disposed at a proximal end thereof to enable rotation of ultrasonic transducer 320 relative to generator 310.

Referring again to FIGS. 1-5, elongated assembly 200 includes a drive member and a support member such as, for example, an outer drive sleeve 210 and an inner support sleeve 220 disposed within outer drive sleeve 210 (although this configuration may be reversed, e.g., wherein the outer sleeve is the fixed support sleeve and the inner sleeve is the movable drive sleeve and/or other suitable drive and support structures, e.g., cables, bars, etc. may be utilized). Elongated assembly 200 further includes a waveguide 230 extending through inner support sleeve 220, a torque adapter 240 engaged about waveguide 230, a drive assembly 250 disposed about outer drive sleeve 210 and operably coupled between outer drive sleeve 210 and bifurcated drive portion 132 of clamp lever 130, a torque housing 260 disposed about outer drive sleeve 210 and operably coupled to waveguide 230, a rotation knob 270 operably disposed about torque housing 260, and an end effector 280 disposed at the distal end of inner support sleeve 220. Elongated assembly 200 is operably engaged with handle assembly 100 such that mechanical motion output from horn 324 of ultrasonic transducer 320 is transmitted along waveguide 230 to end effector 280 for treating tissue therewith, such that clamp lever 130 is selectively actuatable to manipulate end effector 280, and such that rotation knob 270 is selectively rotatable to rotate elongated assembly 200 relative to handle assembly 100.

Outer drive sleeve 210, as noted above, is slidably disposed about inner support sleeve 220. Sleeves 210, 220 may be concentrically arranged about one another and/or waveguide 230. Outer drive sleeve 210 includes drive tube 252 of drive assembly 250 fixedly engaged thereabout. Outer drive sleeve 210 and inner support sleeve 220 are each operably coupled to clamp jaw 282 of end effector 280 at the distal end thereof. More specifically, clamp jaw 282 includes a pair of jaw flanges 284 that are pivotably mounted at the distal end of inner support sleeve 220 to pivotably couple clamp jaw 282 to inner support sleeve 220, and a jaw foot 286 extending through an aperture 214 defined within outer drive sleeve 210 at the distal end thereof such that proximal translation of outer drive sleeve 210 about inner support sleeve 220 and relative to end effector 280 pivots clamp jaw 282 from an open position to a clamping position. Clamp jaw 282 includes a structural body 288 (FIG. 6) supporting a more-compliant jaw liner 290 (FIG. 6) formed from, for example, PTFE. The jaw liner 290 (FIG. 6) of clamp jaw 282 is configured to oppose blade 234 to enable clamping of tissue therebetween.

Waveguide 230, as noted above, extends through inner support sleeve 220. Waveguide 230 defines a body 232, a blade 234 extending from the distal end of body 232, and a proximal connector 239 extending from the proximal end of body 232. Blade 234 extends distally from inner support sleeve 220 and forms part of end effector 280 in that blade 234 is positioned to oppose clamp jaw 282 such that pivoting of clamp jaw 282 from the open position to the clamping position enables clamping of tissue between clamp jaw 282 and blade 234. Blade 234 defines a curved configuration wherein the directions of movement of clamp jaw 282 between the open and clamping positions are perpendicular to the direction of curvature of blade 234. However, it is also contemplated that blade 234 define a straight configuration or that blade 234 curve towards or away from clamp jaw 282, that is, where the directions of movement of clamp jaw 282 between the open and clamping positions are coaxial or parallel to the direction of curvature of blade 234. Multiple curves and/or angles of blade 234 in similar or different directions and/or planes are also contemplated.

Proximal connector 239 of waveguide 230 is configured to enable engagement of waveguide 230 with horn 324 of ultrasonic transducer 320 such that mechanical motion produced by ultrasonic transducer 320 is capable of being transmitted along waveguide 230 to blade 234 for treating tissue clamping between blade 234 and clamp jaw 282 or positioned adjacent to blade 234. To this end, proximal connector 239 includes, for example, a threaded male shaft, that is configured for engagement, e.g., threaded engagement, within female receiver 326 of horn 324 of ultrasonic transducer 320, although other suitable engagement configurations for operably coupling horn 324 and waveguide 230 with one another are also contemplated.

Continuing with reference to FIGS. 1-5, torque adapter 240, as noted above, is engaged about waveguide 230. Torque adapter 240 enables rotational locking of waveguide 230 relative to outer drive sleeve 210, inner support sleeve 220, drive assembly 250, torque housing 260, and rotation knob 270 such that these components rotate together relative to handle assembly 100 upon manipulation of rotation knob 270. Torque housing 260 is configured for engagement about drive tube 252 and functions as an integrated torque-wrench that ensures appropriate application of torque to sufficiently engage waveguide 230 and ultrasonic transducer 320 to one another during assembly, e.g., upon rotation of rotation knob 270 relative to ultrasonic transducer 320, while inhibiting over-tightening of the engagement between waveguide 230 and ultrasonic transducer 320, e.g., despite further rotation of rotation knob 270 relative to ultrasonic transducer 320.

Drive assembly 250 of elongated assembly 200 is disposed about outer drive sleeve 210 and operably coupled between outer drive sleeve 210 and bifurcated drive portion 132 of clamp lever 130. Drive assembly 250 includes a drive tube 252 and a rigid slider 256. Drive tube 252 is fixedly engaged about outer drive sleeve 210 and includes a distal collar 253a and a proximal body 253b. Rigid slider 256 includes an inner retainer 254 fixedly engaged with proximal body 253b of drive tube 252 at a proximal end portion thereof and an outer slider 258 slidably disposed about a distal body 259b of inner retainer 254 between a proximal rim 259a of inner retainer 254 and distal collar 253a of drive tube 252. Alternatively or additionally, distal body 259b of inner retainer 254 may be omitted or shortened such that outer slider 258 is slidably disposed proximal body 253b of drive tube 252.

In some configurations, rather than outer slider 258 of rigid slider 256 being slidable relative to inner retainer 254, outer slider 258 and inner retainer 254 may be fixed relative to one another, e.g., via a fixed engagement (such as by welding, snap-fitting, interference fitting, keyed engagement, adhesion, etc.), or via monolithically forming as a single component. In some configurations, rigid slider 256 (or a portion thereof) is monolithically formed with drive tube 252. In still other configurations, drive tube 252 is omitted and rigid slider 256 is directly coupled about a proximal end portion of outer drive sleeve 210. In configurations where rigid slider 256 is directly coupled about outer drive sleeve 210, inner retainer 254 may be fixed about outer drive sleeve 210, e.g., via welding, snap-fitting, interference fitting, keyed engagement, adhesion, etc., or via monolithic formation, while outer slider 258 is slidable relative to both inner retainer 254 and outer drive sleeve 210, or both inner retainer 254 and outer slider 258 may be fixed relative to outer drive sleeve 210.

Inner retainer 254 and outer slider 258 of rigid slider 256 may be formed from any (similar or different) substantially rigid material or materials such that rigid slider 256 is not configured to compress, extend, or otherwise deflect during normal operation. Further, rigid slider 256 is configured to provide a 1:1 force ratio; that is, a force input to rigid slider 256 is substantially equal to a force output from rigid slider 256 (due to the lack of compression, extension, etc. thereof). Thus, rigid slider 256 is configured to transfer force without itself limiting or otherwise modifying force.

An annular gap 255 (FIG. 5) is defined about distal body 259b of inner retainer 254 or, in configurations where distal body 259b is omitted or shortened, about proximal body 253b of drive tube 252. Annular gap 255 is defined longitudinally between the distal end of outer slider 258 of rigid slider 256 and distal collar 253a of drive tube 252 and is configured to receive bifurcated drive portion 132 of clamp lever 130 on either side thereof such that actuation of clamp lever 130 urges rigid slider 256. More specifically, proximal and distal contact surfaces 136, 138 of clamp lever 130 are configured for positioning within annular gap 255 adjacent the distal end of outer slider 258 of rigid slider 256 and distal collar 253a of drive tube 252, respectively, such that proximal actuation of clamp lever 130 urges proximal contact surface 136 into the distal end of outer slider 258 to thereby urge outer slider 258 proximally. Outer slider 258, in turn, whether by fixed engagement or by sliding contact, urges inner retainer 254 proximally to thereby urge drive tube 252 and outer drive sleeve 210 proximally. Of course, where drive tube 252 is omitted, the proximal movement of inner retainer 254 directly urges outer drive sleeve 210 proximally. In either configuration, proximal movement of outer drive sleeve 210, as noted above, pivots clamp jaw 282 from the open position towards the clamping position for clamping tissue between clamp jaw 282 and blade 234. Distal return of clamp lever 130, on the other hand, urges distal contact surface 138 into contact with raised collar 253a of drive tube 252 (or other feature associated with rigid slider 256 or outer drive sleeve 210) to thereby urge outer drive sleeve 210 distally to return clamp jaw 282 back towards the open position.

The longitudinal length of annular gap 255, e.g., the distance between the distal end of outer slider 258 of rigid slider 256 and distal collar 253a of drive tube 252 substantially approximates the distance between proximal and distal contact surfaces 136, 138 to substantially eliminate any play therebetween while permitting bifurcated drive portion 132 of clamp lever 130 to pivot within annular gap 255 as clamp lever 130 is pivoted relative to body portion 112 of housing 110 about pivot axis 134.

As an alternative to the above-detailed configuration, wherein proximal translation of outer drive sleeve 210 in response to proximal pivoting of bifurcated drive portion 132 of clamp lever 130 pivots clamp jaw 282 from the open position to the clamping position, the opposite configuration may be provided, such as detailed below with respect to FIG. 11.

Continuing with reference to FIGS. 1-5, as noted above, clamp lever 130 and drive assembly 250 are designed such that the force imparted to clamp lever 130 is proportional to the longitudinal motion of outer drive sleeve 210 to pivot clamp jaw 282 from the open position towards the clamping position for clamping tissue between clamp jaw 282 and blade 234 under a clamping force and, thus, such that the lever force imparted to clamp lever 130 is proportional to the jaw force applied by clamp jaw 282 (and the jaw pressure applied by clamp jaw 282). Although there is necessarily some dampening and/or loss from connections, friction, material properties, etc., associated with clamp lever 130, waveguide 230, and drive assembly 250, neither clamp lever 130, waveguide 230, nor drive assembly 250 is designed to incorporate any specific force-dampening features such as, for example: increased flexibility or a spring incorporated into a portion(s) of clamp lever 130, one or more springs associated with drive assembly 250, increased flexibility or a spring incorporated into a portion(s) of drive sleeve 210, increased flexibility or a spring incorporated into a portion(s) of waveguide 230, other flexible connections specifically designed to dampen force, etc.

Rather than using one or more springs, flexible portions, flexible connections, and/or other suitable dampening feature(s) to regulate the jaw force (and jaw pressure) applied by clamp jaw 282, ultrasonic instrument 10 (FIG. 1) as a whole and, more specifically, clamp lever 130 and drive assembly 250 thereof, are design to provide substantially no dampening between clamp lever 130 and clamp jaw 282, and are tuned to provide a jaw force (defined herein as a numerical jaw force or jaw force within a numerical range), to require a lever force (defined herein as a numerical lever force or lever force within a numerical range), and/or to provide a jaw pressure (defined herein as a numerical jaw pressure or jaw pressure within a numerical range). As detailed below, the jaw force and/or lever force may be based on fully-actuating clamp lever 130, e.g., wherein grasping portion 131 of clamp lever 130 contacts fixed handle portion 114 of housing 110 (or at another hard stop), while clamp jaw 282 is clamped against a test device (and is not in contact with blade 234). However, other suitable bases for determining the jaw force and lever force are also contemplated. It is noted that the jaw force and lever force to which ultrasonic instrument 10 (FIG. 1) is turned are not necessarily the forces applied during use but, rather, are set points based upon which ultrasonic instrument 10 (FIG. 1) is designed and based upon which ultrasonic instrument 10 (FIG. 1) can be tested during manufacturing to ensure compliance. Further, the values of such forces are not universal but, rather, are relative to the manner in which the forces are measured. As such, the present disclosure is not limited to particular set point forces or manners of determining the same but, rather, is inclusive of any suitable forces and/or manners of determining the same to which an ultrasonic surgical instrument can be readily tuned. Further, an acceptable tolerance level may be built into the forces to allow for acceptable variation, e.g., due to manufacturing tolerances, material tolerances, use and environmental tolerances, measurement variations, and/or other variations, in the design and manufacturing of ultrasonic surgical instrument 10 (FIG. 1). An acceptable tolerance may include, for example, plus or minus 10% of the force(s), although other acceptable tolerances are also contemplated.

Jaw pressure may correspond to the pressure applied by clamp jaw 282 to tissue, e.g., a blood vessel, clamped between clamp jaw 282 and blade 234 during use and/or in testing, and may be based on fully-actuating clamp lever 130, e.g., wherein grasping portion 131 of clamp lever 130 contacts fixed handle portion 114 of housing 110 (or at another hard stop). Further, with respect to testing, a tissue-approximating structure such as, for example, a rubber pad, a foam pad, an elastic tube, etc., may be utilized in place of actual tissue. Jaw pressure is calculated as jaw force divided by clamping surface area. The jaw force may be an average jaw force applied to tissue (or a tissue-approximating structure) clamped between clamp jaw 282 and blade 234, e.g., an average of plural measurements taken at plural locations along the tissue-contacting length of blade 234 such as, for example, at a proximal heal location, a distal tip location, and an intermediate location, thus yielding an average jaw pressure. Alternatively, the jaw force may be measured at a single, pre-defined location, e.g., at a midpoint.

As pressure is force per unit area, for the same force applied, the pressure applied to tissue that contacts the entire clamping surface area is less than the pressure applied to tissue that contacts only a portion of the clamping surface area. The pressures detailed herein are based on tissue contacting the entire clamping surface area. The clamping surface area is defined as the tissue-contacting surface area of jaw liner 290 (FIG. 6) that clamps tissue against the blade 234 in the clamping position, e.g., a length of the tissue-contacting surface of jaw liner 290 (FIG. 6) that extends along the blade 234 multiplied by a width of the tissue-contacting surface of jaw liner 290 (FIG. 6) that extends across the blade 234. Jaw pressure may alternatively be calculated by dividing the set-point jaw force, e.g., as detailed herein (instead of measuring a jaw force applied to clamped tissue), by the clamping surface area. The clamping surface area may be, in aspects, from about 0.020 in$^2$ to about 0.040 in$^2$; in other aspects, from about 0.025 in$^2$ to about 0.035 in$^2$; and, in still other aspects, about 0.028 in$^2$, although other clamping surface areas are also contemplated depending, for example, upon the tissue effect desired, the waveguide configuration, the blade configuration, the operating parameters, etc.

Figure 6:
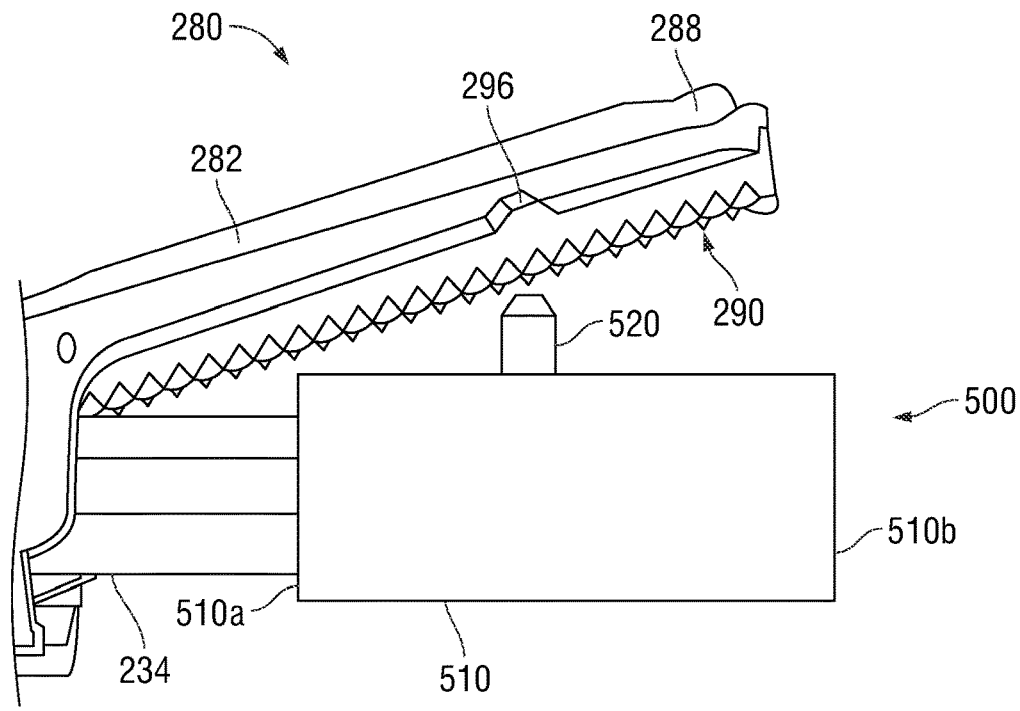
FIG. 6 is an enlarged, perspective view of an end effector of the ultrasonic surgical instrument of FIG. 1 operably coupled to a jaw force test fixture.
Figure 7:
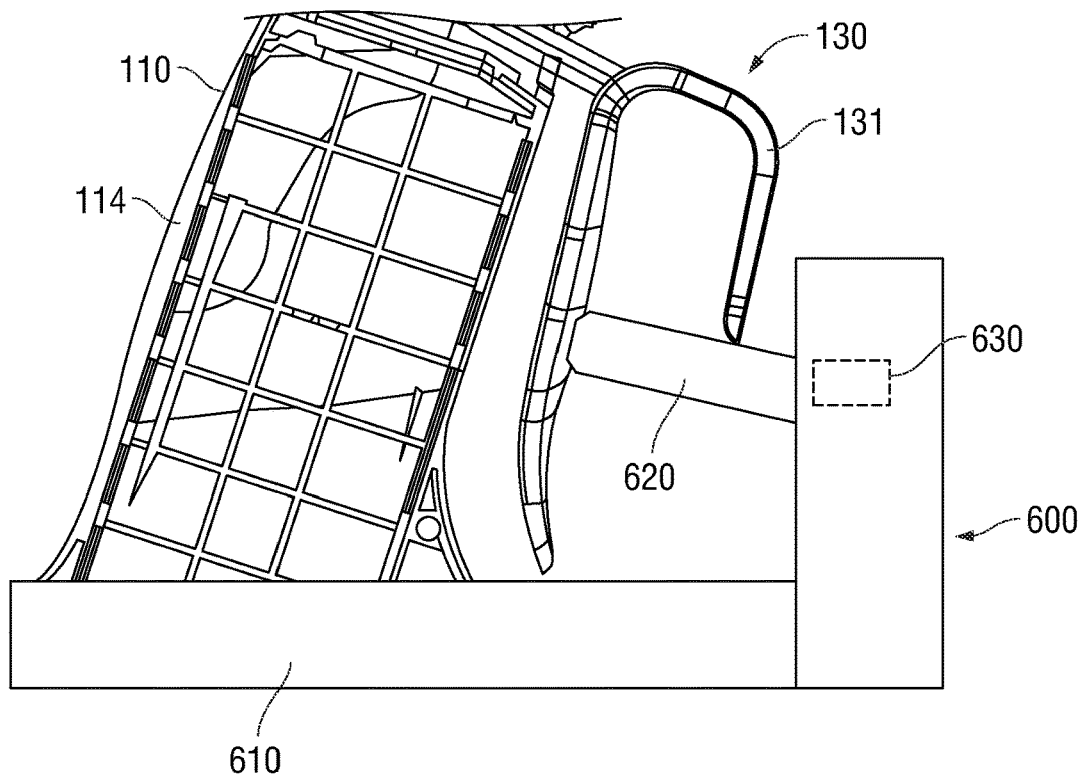
FIG. 7 is an enlarged, perspective view of a portion of the ultrasonic surgical instrument of FIG. 1 including the fixed handle portion and clamp lever operably coupled to a lever force test fixture.

Referring to FIGS. 6 and 7, exemplary set-ups for measuring the set point jaw force and lever force, respectively, are shown, although other suitable configurations are also contemplated. With initial reference to FIG. 6, end effector 280 of ultrasonic surgical instrument 10 is shown disposed within a testing assembly 500. Testing assembly 500 generally includes a fixture 510 and a sensor 520 coupled to fixture 510. Fixture 510 defines a longitudinal channel extending from a proximal end portion 510*a* to a distal end portion 510*b* of fixture 510 to enable receipt and retention of blade 234 of end effector 280 therein. End effector 280, more specifically, is positioned relative to fixture 510 such that sensor 520 is disposed adjacent a notch 296 defined within structural body 288 of clamp jaw 282. As a result of this configuration, as clamp jaw 282 is approximated relative to blade 234, sensor 520 is received within notch 296, wherein sensor 520 measures the jaw force applied by clamp jaw 282. Sensor 520 may be, for example, a force sensor, e.g., a load cell, or any other suitable sensor capable of measuring and providing feedback with respect to the jaw force applied by clamp jaw 282 of end effector 280. It is noted that sensor 520 is received within notch 296 and measures the jaw force when clamp lever 130 is in the fully actuated position (without jaw liner 290 contacting blade 234), although other configurations are also contemplated such as, for example the omission of notch 296. Whether notch 296 is provided or not, sensor 520 is configured to obtain a jaw force measurement provided by structural body 288 at a known longitudinal position such as, for example, a distance of about 0.192 inches from a distal end of clamp jaw 282. In aspects, jaw force is measured at multiple locations, e.g., at a proximal end portion of clamp jaw 282, a distal end portion of clamp jaw 282, and an intermediate position therebetween, to enable determination of an average jaw force along the length of structural body 288. Further, as another alternative to providing a notch 296, sensor 520, another sensor (not shown), or a manual measurement may utilized to measure a distance from the measurement point to the pivot location of clamp jaw 282 and/or to the distal end of clamp jaw 282 to enable normalization of the jaw force measurement across different device configurations. With respect to measuring jaw force in use or in testing to simulate use on tissue, sensor 520 may be incorporated into tissue or a tissue-approximating structure that is clamped between clamp jaw 282 and blade 284 in order to enable measurement of the jaw force applied thereto, e.g., at one or more locations. Regardless of the manner in which the jaw force measurement taken, jaw pressure may be determined based thereon by dividing the jaw force by the clamping surface area. Where multiple jaw force measurements are used to determine an average jaw force, an average jaw pressure may thus be determined.

Turning to FIG. 7, fixed handle portion 114 of ultrasonic surgical instrument 10 is shown disposed within a testing assembly 600. Testing assembly 600 generally includes a fixture 610, a piston 620, and a sensor 630 configured to measure a force applied by piston 620. Fixture 610 is configured to retain a portion of fixed handle portion 114 therein and operably supports piston 620 thereon. Piston 620 is positioned distally adjacent grasping portion 131 of clamp lever 130 and is configured, upon activation, to actuate clamp lever 130, e.g., urging clamp lever 130 proximally. Sensor 630 is configured to measure the force required to urge clamp lever 130 to a fully-actuated position, e.g., wherein at least a portion of grasping portion 131 of clamp lever 130 abuts fixed handle portion 114, although the fully-actuated position need not require such contact and/or other reference positions for determining lever force may also be utilized. Piston 620 is positioned to contact clamp lever 130 at about a midpoint along the height of grasping portion 131 of clamp lever 130, adjacent the free end of the hook portion of clamp lever 130, although other configurations are also contemplated.

Referring generally to FIGS. 1-5, utilizing a rigid configuration wherein clamp lever 130 and drive assembly 250 are tuned to achieve a lever force, jaw force, and/or jaw pressure is advantageous at least because such a configuration enables more precise tuning, reduces cost and complexity, and also provides increased tactility in that it enables the user to feel the amount of jaw force applied. The use of a spring(s) or other dampening feature(s), on the other hand, dampens the tactility between the user and tissue, can be challenging for manufacturing, and adds additional cost and complexity to the mechanical system.

Altering the configuration of one or more components of ultrasonic instrument 10 enables ultrasonic instrument 10 (FIG. 1) and, more specifically, clamp lever 130 and drive assembly 250, to be tuned to achieve the desired lever force, jaw force, and/or jaw pressure. For example, moving the position of proximal contact surface 136 proximally or distally (along a longitudinal axis defined through outer drive sleeve 210) alters the jaw force (and, thus, the jaw pressure). More specifically, moving proximal contact surface 136 proximally reduces the jaw force while moving the proximal contact surface 136 distally increases the jaw force. Proximal contact surface 136 may be moved by modifying a width of bifurcated drive portion 132 at proximal contact surface 136 or in any other suitable manner. Modifying the position of proximal contact surface 136 may also require further modification of bifurcated drive portion 132 and, more specifically, the longitudinal position of distal contact surface 138, to maintain bifurcated drive portion 132 within annular gap 255 to substantially eliminate any play therebetween.

Figure 8A:
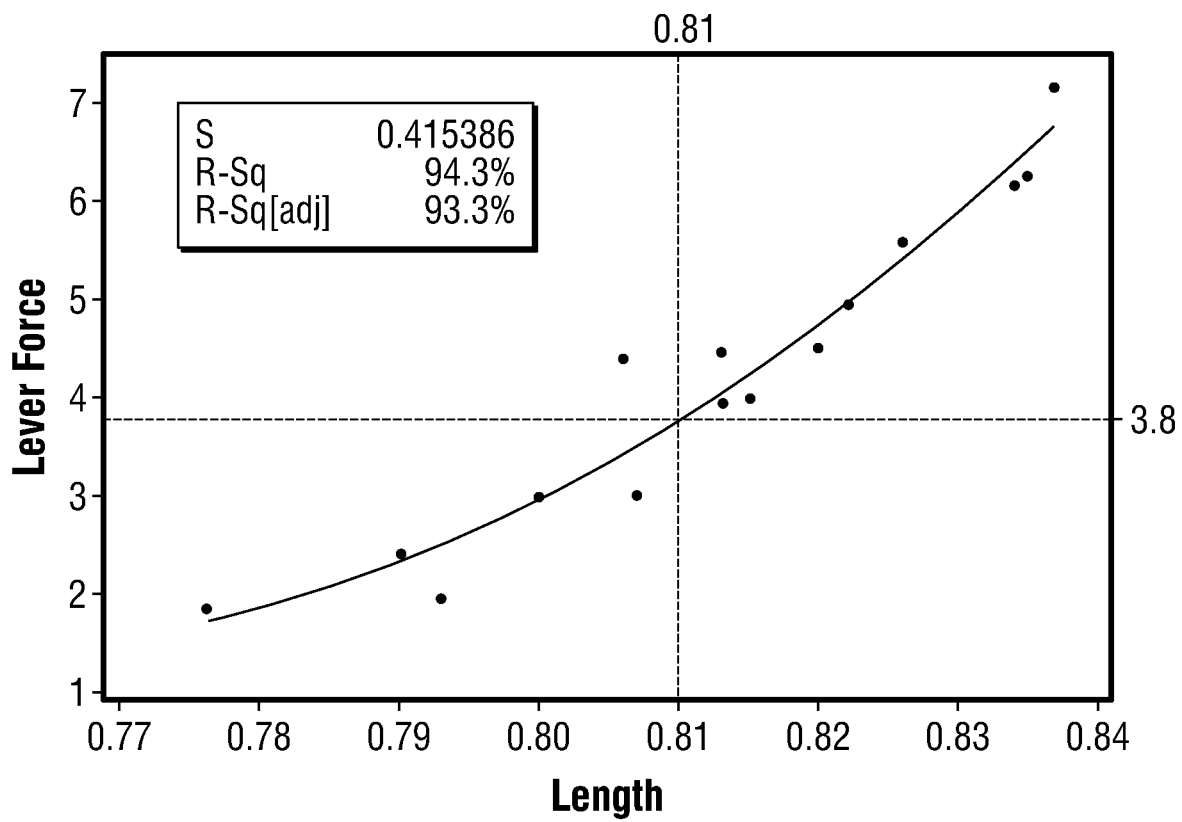
FIGS. 8A and 8B are experimental result graphs of lever force versus length and jaw force versus length, respectively, in accordance with the present disclosure.
Figure 8B:
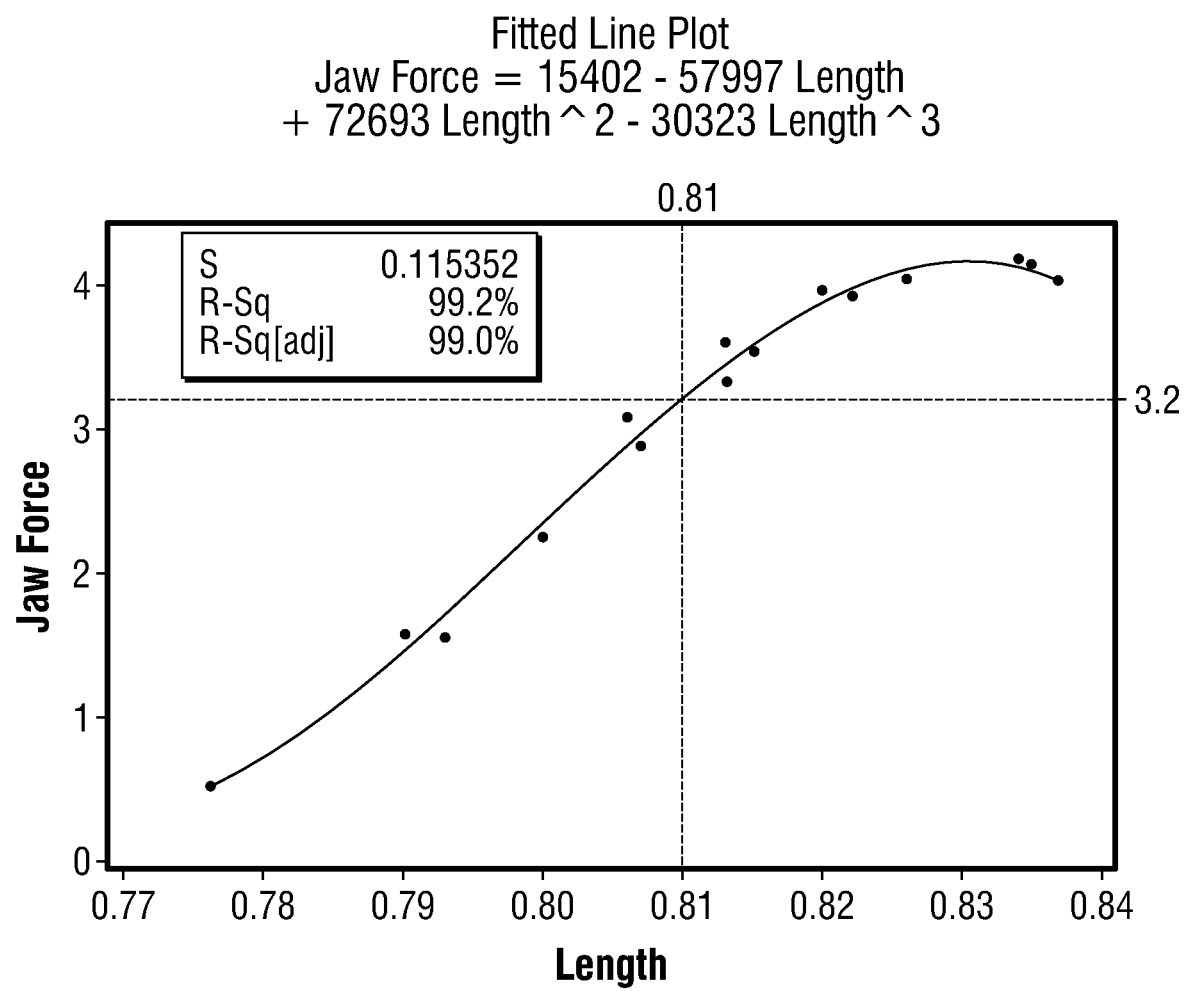

As another example, instead of or in addition to modifying a width of bifurcated drive portion 132 at proximal contact surface 136, the longitudinal length of outer slider 258 of rigid slider 256 may be modified. More specifically, increasing the length of outer slider 258 increases the jaw force (and, thus, the jaw pressure) and the lever force, while decreasing the length of outer slider 258 decreases the jaw force (and, thus, the jaw pressure) and the lever force. Experimental results illustrating the same are shown in FIGS. 8A and 8B. By way of example, and as illustrated in the graphs of FIGS. 8A and 8B, the length of outer slider 258 (and/or configurations of other components) may be tuned to achieve a lever force of about 3.8 lbf and/or a jaw force of about 3.2 lbf, although outer suitable forces (including force ranges) are also contemplated. For example, the lever force may be from about 1 lbf to about 10 lbf; in other aspects, from about 2 lbf to about 5 lbf. The jaw force may be from about 1 lbf to about 8 lbf; in other aspects, from about 2 lbf to about 5 lbf; in still other aspects from about 2.5 lbf to about 4.5 lbf. The jaw pressure may be from about 35 psi to about 285 psi; in other aspects, from about 70 psi to about 180 psi; and in other aspects from about 90 psi to about 160 psi.

Figure 9A:
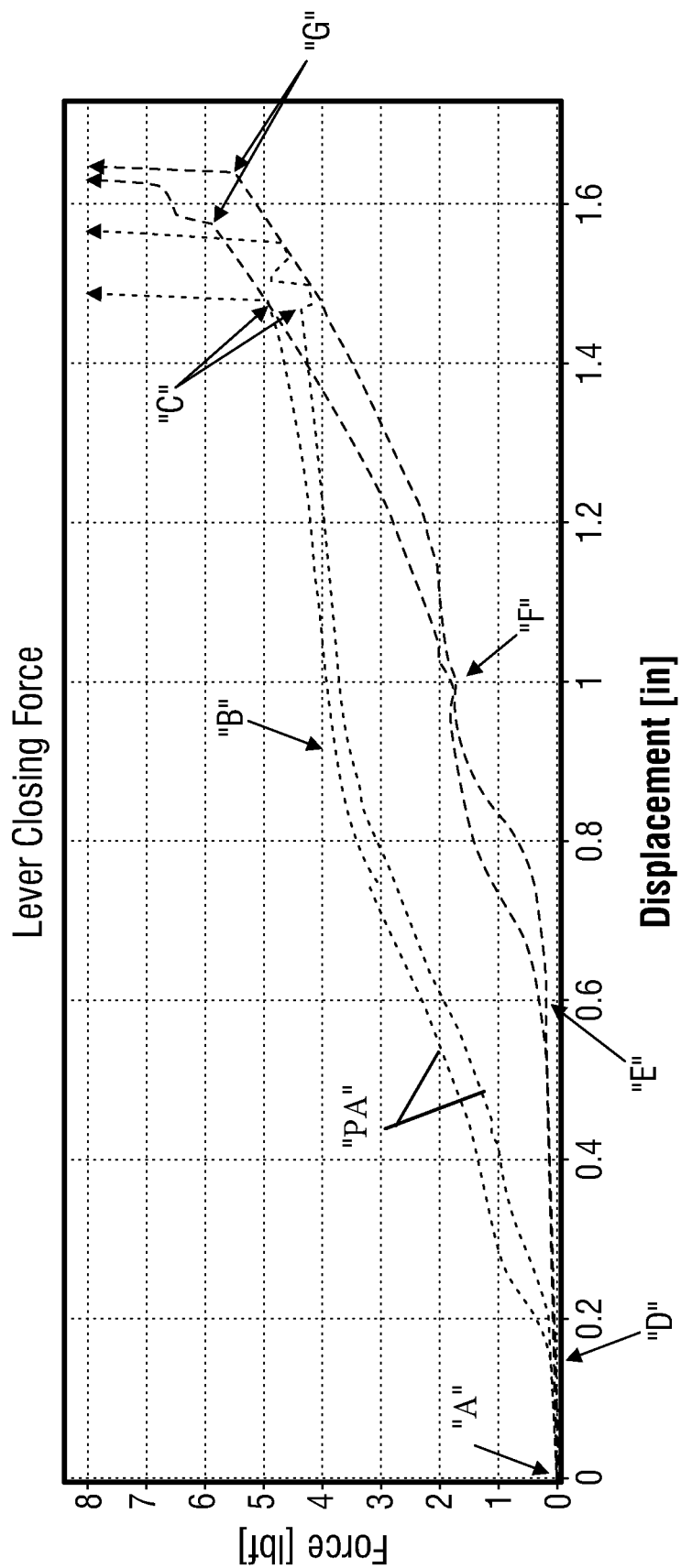
FIG. 9A is an experimental result graph of lever force versus lever displacement for prior art devices and devices in accordance with the present disclosure.

Turning to FIG. 9A, experimental results illustrating clamp lever force as a function of clamp lever displacement, e.g., from the un-actuated position towards the actuated position, are shown for a prior art device including a force-dampening spring ("PA") and for a device employing a rigid configuration in accordance with the present disclosure ("PD"). The clamp lever force measurements were obtained using a structure clamped between the jaw and blade that approximates tissue, e.g., a rubber pad, and has a sufficient thickness to approximate a substantially full grasp of tissue between the jaw and blade. Further, it is noted that the plotted lines are offset for clarity, e.g., the "PA" and "PD" lines do not start at zero force/displacement.

With respect to the plotted lines indicative of the prior art "PA," the slope between points "A" and "B" is defined by waveguide deflection, tissue compression, and a relatively minor influence of the force-dampening spring. Between points "B" and "C," the slope is defined by the compression of the dampening spring with relatively minor influence from tissue compression and system tolerances. At point "C," the clamp lever is disposed in the fully actuated position, e.g., at least partially contacting the fixed handle.

With respect to the plotted lines indicative of the present disclosure "PD," the slope between point "D" and point "E" is substantially zero (with any slope attributed thereto being an artifact of the experimental set up). The slope between point "E" and point "F" is defined by waveguide deflection, tissue compression, and a relatively minor influence from system tolerances. The slope from point "F" to point "G" is defined by properties of the tissue, e.g., stiffness, thickness, etc., with minor influence from system tolerances. At point "G," the clamp lever is disposed in the fully actuated position, e.g., at least partially contacting the fixed handle.

Comparing the slope between points "B" and "C" on the plotted lines indicative of the prior art "PA" with the slope between points "E" and "G" on the plotted lines indicative of the present disclosure "PD," it can be seen that the slope between "B" and "C" approaches zero, providing little to no "feel" to the user, while the slope between points "E" and "G" is angled and, thus, provides the user with a near real "feel" of force input (by the clamp lever) to force applied (to tissue). From this "feel," the user gains knowledge of the thickness, hardness, etc. of tissue being clamped between the jaw and blade. Further, due to the effects of the dampening spring in the prior art devices, the slope between "B" and "C" remains substantially consistent, approaching zero, regardless of tissue thickness, hardness, etc., thus providing little to no feedback relating to these tissue properties. The slope between points "E" and "G" varies between a shallower angle and a steeper angle depending upon the tissue properties (thickness, hardness, etc.), thus providing the feedback regarding the same, e.g., in the form of "feel" to the user.

Figure 9B:
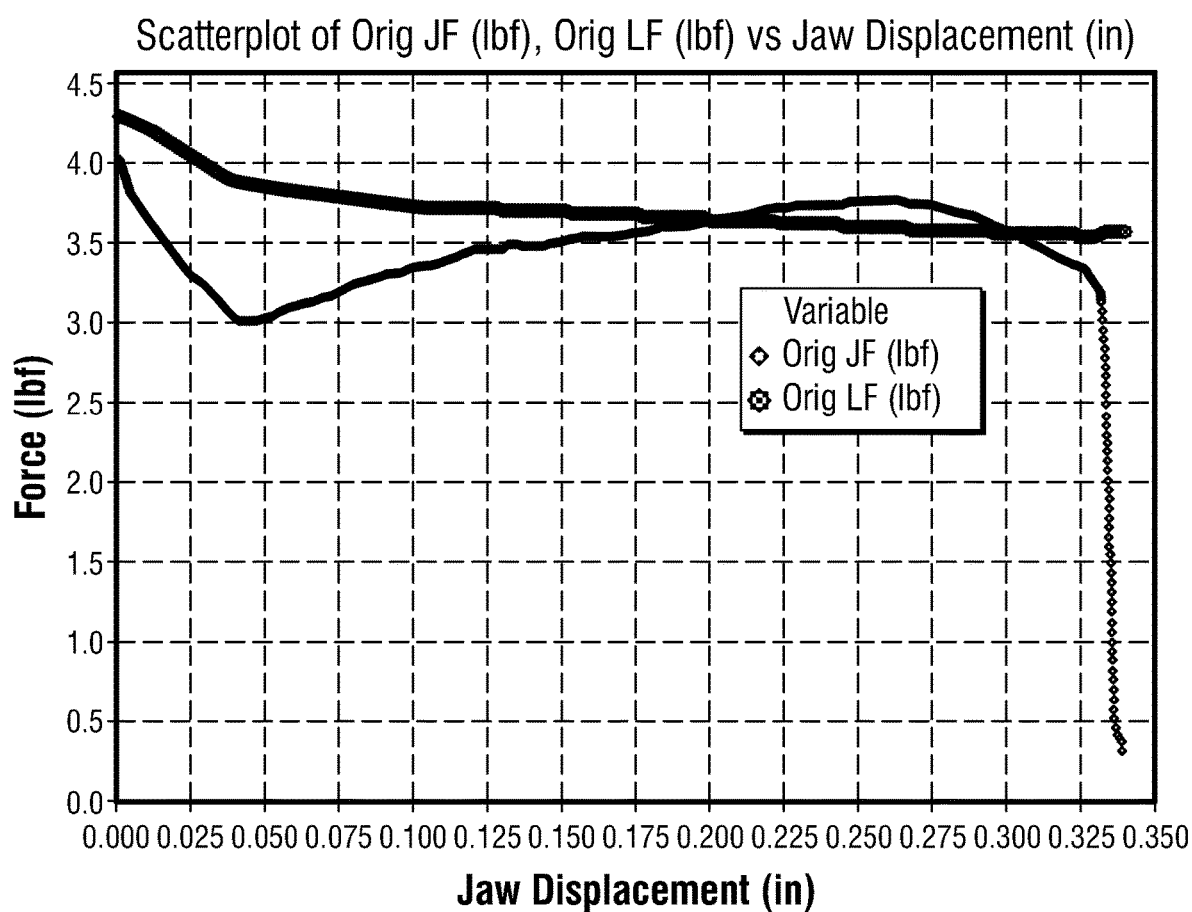
FIGS. 9B and 9C are experimental result graphs of clamp lever force and jaw force as a function of clamp jaw displacement for prior art devices and devices in accordance with the present disclosure, respectively.
Figure 9C:
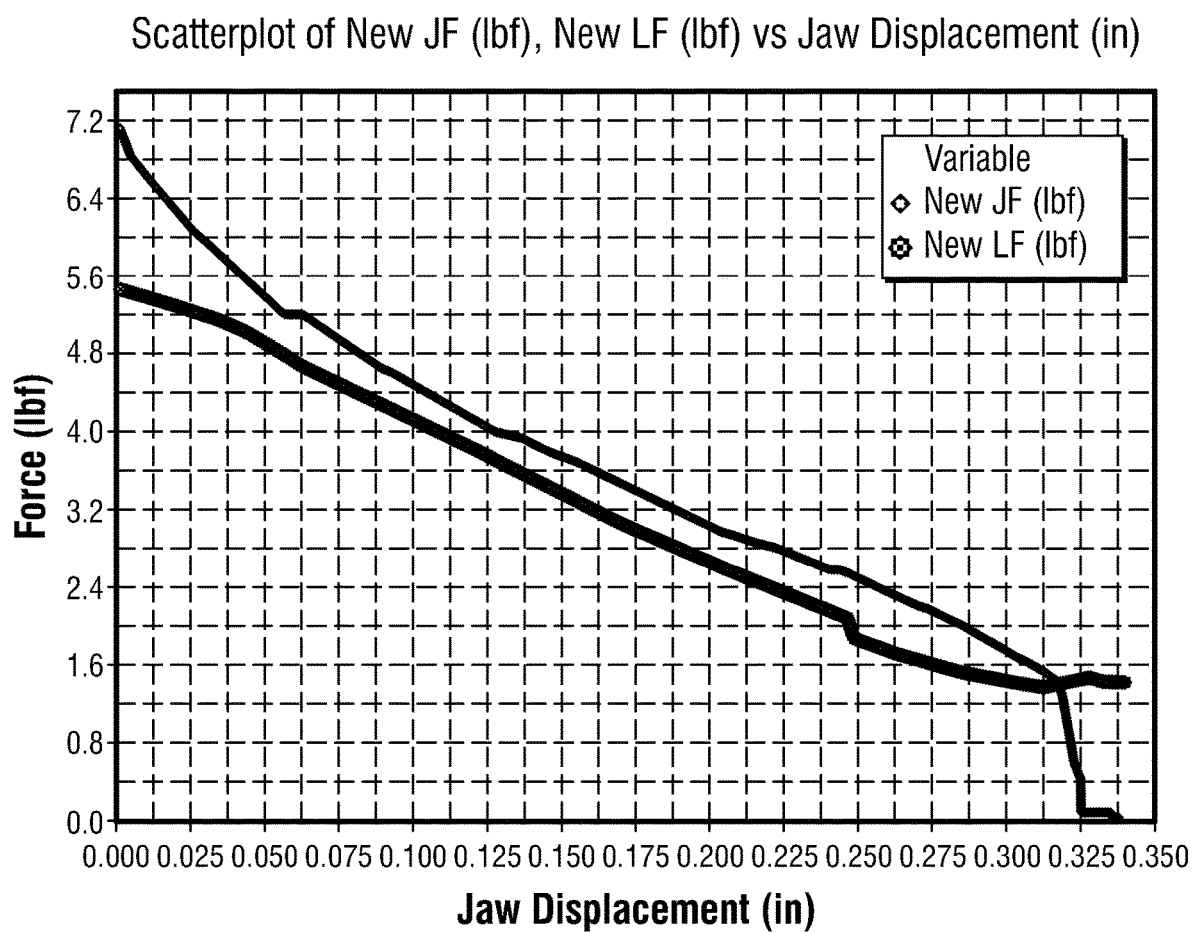

With reference to FIGS. 9B and 9C, experimental results illustrating clamp lever force and jaw force as a function of clamp jaw displacement, e.g., from the open position towards the clamping position, are shown for prior art devices including force-dampening springs (FIG. 9B) and for c in accordance with the present disclosure (FIG. 9C). On the graphs, zero displacement corresponds to the open position of the clamp jaw, with displacement increasing as the clamp jaw is pivoted towards the clamping position. The drop offs in jaw force indicated on the far right of the graphs correspond to the fully clamped position, at approximately 0.325 inches of jaw displacement. These experimental results were obtained by initially clamping the clamp jaw on a first load cell in a fully open position with the clamp lever disposed in a fully actuated position. A second load cell constrained the lever in the fully actuated position. The clamp jaw was then incrementally moved from the fully open position to the fully clamped position. Data was collected off both load cells are the various incremental positions of the clamp jaw between the fully open position and the fully clamped position to obtain the jaw force and lever force data shown in FIGS. 9B and 9C.

As shown in FIG. 9B, due to the force-dampening springs utilized in the prior art devices, the jaw force and lever force remain substantially constant as the clamp jaw is pivoted towards the fully clamped position. In contrast, as shown in FIG. 9C, with respect to the devices of the present disclosure employing a rigid configuration, both the jaw force and the lever force varied (e.g., decreased substantially linearly) as the clamp jaw was pivoted towards the fully clamped position. Thus, the devices of the present disclosure provide feedback to the user, as varying lever force, as to position of the clamp jaw and/or the jaw force applied thereby. No such feedback is provided by the prior art devices.

Returning to FIGS. 1-5, as still another example, the radial distance between pivot axis 134 and proximal contact surface 136 may be varied to modify the requisite lever force required to fully actuate clamp lever 130 (e.g., to achieve the jaw force (and, thus, the jaw pressure)). More specifically, decreasing the distance between pivot axis 134 and proximal contact surface 136 decreases the lever force while increasing the distance increases the lever force.

Figure 10:
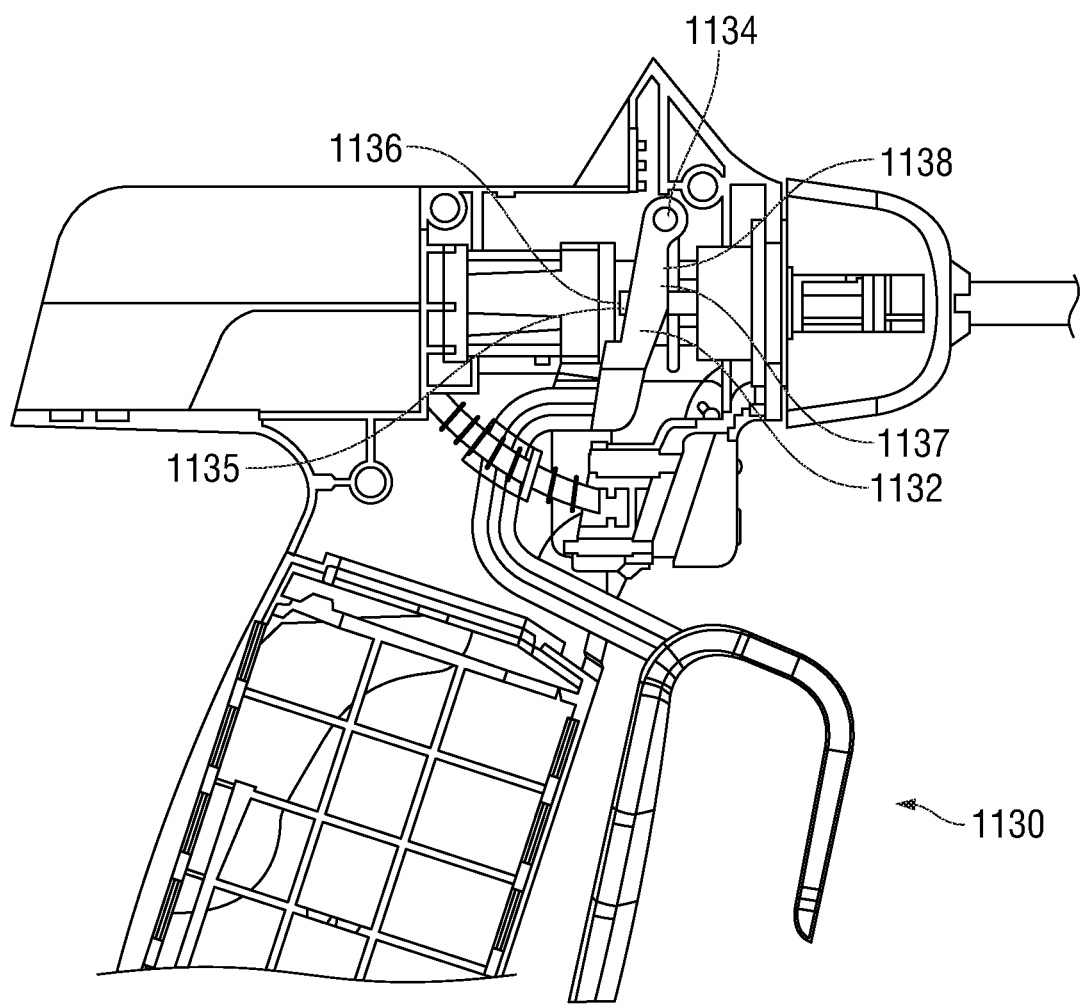
FIG. 10 is a side view of the ultrasonic surgical instrument of FIG. 1 as illustrated in FIG. 5, including another clamp lever in accordance with the present disclosure.

With reference to FIG. 10, another clamp lever 1130 provided in accordance with the present disclosure is shown wherein bifurcated drive portion 1132 includes a proximally-extending protrusion 1135 defining proximal contact surface 1136 and a distally-extending protrusion 1137 defining distal contact surface 1138. The amounts proximally and distally-extending protrusions 1135, 1137 protrude may be varied as detailed above to achieve lever force and the jaw force. Alternatively or additionally, proximally-extending protrusion 1135 may be moved towards pivot axis 1134 or away from pivot axis 134 (to thereby move proximal contact surface 1136) to achieve the lever force.

Figure 5:
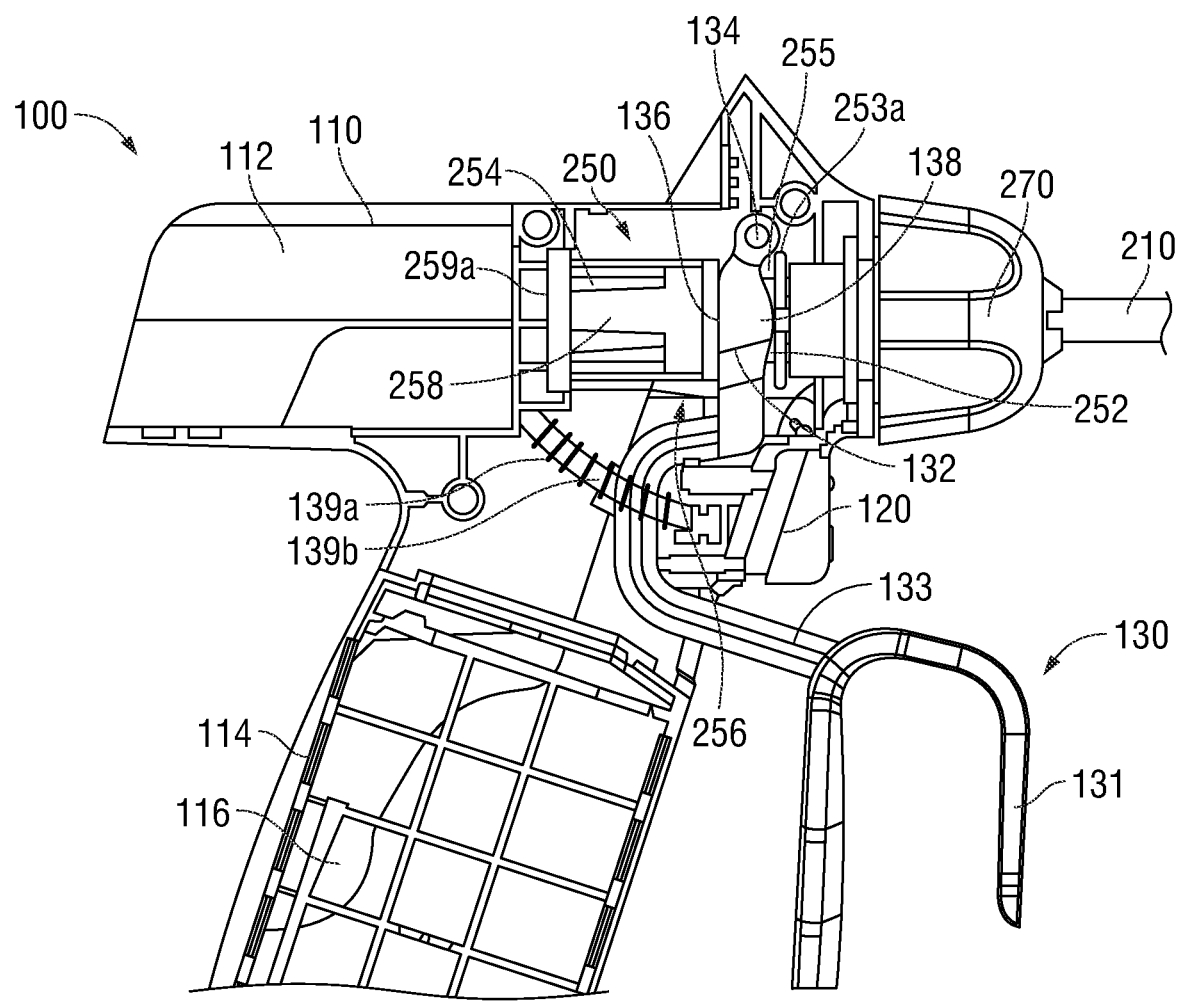
FIG. 5 is a side view of a proximal portion of the ultrasonic surgical instrument of FIG. 1 wherein an outer housing portion, an ultrasonic transducer and generator assembly, a battery assembly, and additional internal component are removed to unobstructively illustrate the operable coupling between a clamp lever and drive assembly of the ultrasonic surgical instrument.
Figure 11:
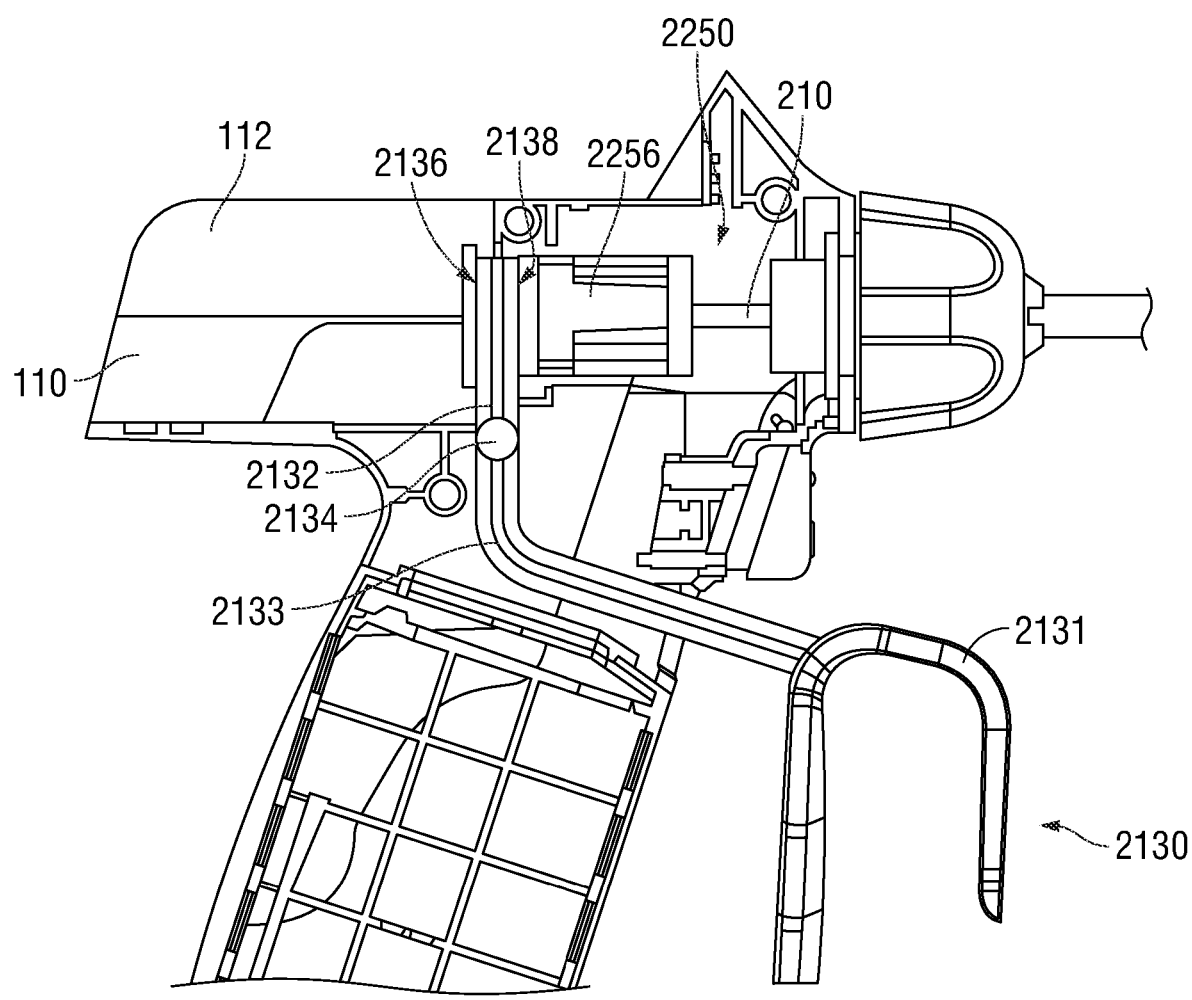
FIG. 11 is a side view of the ultrasonic surgical instrument of FIG. 1 as illustrated in FIG. 5, including another clamp lever and drive assembly in accordance with the present disclosure.

Turning to FIG. 11, in the above-detailed configurations of clamp levers (e.g., clamp levers 130, 1130 (FIGS. 5 and 10, respectively)), lever force and jaw force are positively correlated with respect to modifications to longitudinal positioning of the proximal contact surface and/or length of the rigid slider. That is, the lever force and jaw force are moved in the same direction, e.g., increased or decreased, in response to modifying the longitudinal positioning of the proximal contact surface and/or length of the rigid slider. FIG. 11 illustrates another configuration of clamp lever 2130 and drive assembly 2250 in accordance with the present disclosure wherein the lever force and jaw force are inversely correlated. More specifically, clamp lever 2130 includes a grasping portion 2131 extending from body portion 112 of housing 110, a bifurcated drive portion 2132 extending into body portion 112 of housing 110, and a connector portion 2133 interconnecting grasping portion 2131 and bifurcated drive portion 2132. Clamp lever 2130 is pivotably connected to housing 110 about a pivot axis 2134 that is disposed at connector portion 2133 of clamp lever 2130 between grasping portion 2131 and bifurcated drive portion 2132 and, thus, below a longitudinal axis of outer drive sleeve 210. In this manner, actuation of clamp lever 2130 moves bifurcated drive portion 2132 distally. As such, rigid slider 2256 is positioned distally of bifurcated drive portion 2132 and is oppositely oriented compared to rigid slider 256 (FIG. 5) but may otherwise be configured similarly as rigid slider 256 (FIG. 5). Thus, actuation of clamp lever 2130 translates outer drive sleeve 210 distally to move clamp jaw 282 (FIG. 1) towards the clamping position and to apply the jaw force. The operability of proximal and distal contact surfaces 2136, 2138 of clamp lever 2130 are opposite of those detailed above with respect to configurations wherein the pivot location is above the longitudinal axis and the rigid slider is positioned proximally of the clamp lever. Further, the operable coupling of clamp jaw 282 (FIG. 1) with outer drive sleeve 210 may be modified to accommodate the clamping of clamp jaw 282 (FIG. 1) in response to distal movement of outer drive sleeve 210, e.g., via positioning jaw foot 286 (FIG. 4) on the opposite side of the jaw pivot, utilizing a cam-slot engagement, camming outer drive sleeve 210 about clamp jaw 282 (FIG. 1) to act as a closure tube, or in any other suitable manner.

The above-detailed configuration illustrated in FIG. 11 provides for an inverse correlation between lever force and jaw force with respect to modifications to longitudinal positioning of the distal contact surface and/or length of the rigid slider. That is, in the configuration of clamp lever 2130 and drive assembly 2250 in FIG. 11, as the longitudinal positioning of the proximal contact surface and/or length of the rigid slider is altered, lever force is modified in one direction while jaw force is modified in the opposite direction.

Figure 12:
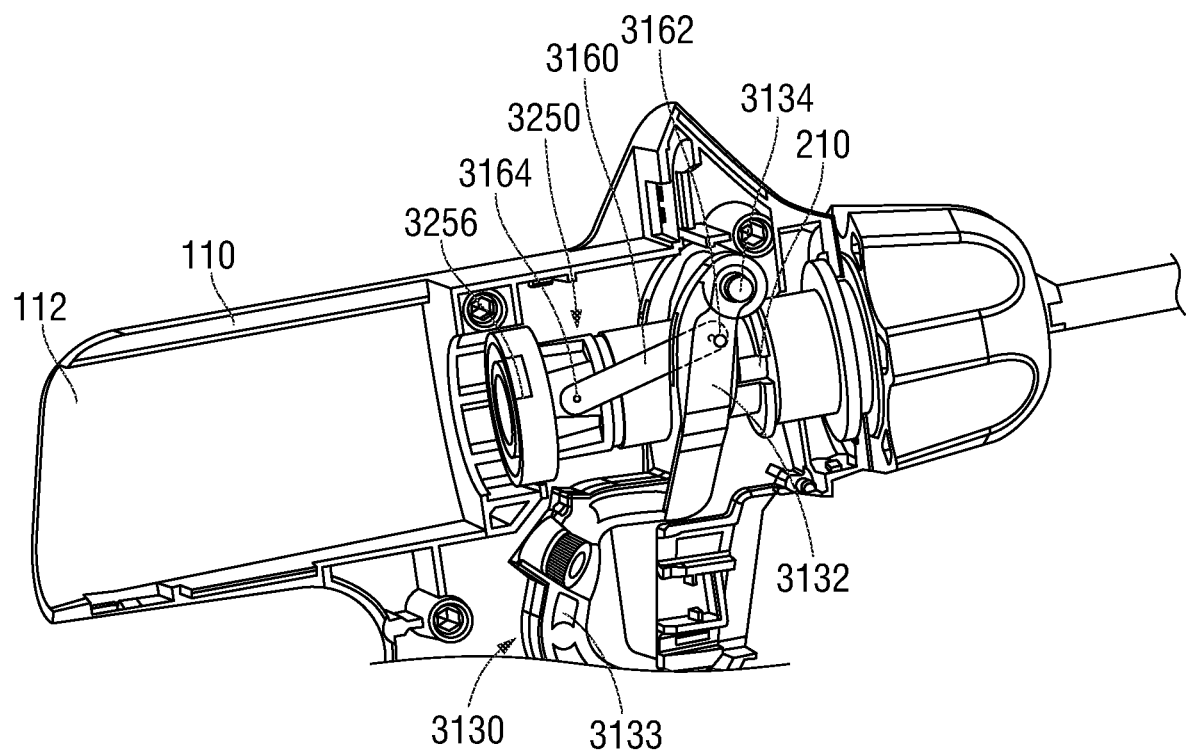
FIG. 12 is a side, perspective view of the ultrasonic surgical instrument of FIG. 1 as illustrated in FIG. 5, including another clamp lever and drive assembly in accordance with the present disclosure.

With reference to FIG. 12, another configuration of clamp lever 3130 and drive assembly 3250 in accordance with the present disclosure is shown wherein, rather than including contact surfaces on clamp lever 3130 to directly interact with drive assembly 3250, first and second linkages 3160 operably couple clamp lever 3130 with rigid slider 3256 of drive assembly 3250. More specifically, clamp lever 3130 includes a grasping portion (not shown) extending from body portion 112 of housing 110, a bifurcated drive portion 3132 extending into body portion 112 of housing 110, and a connector portion 3133 interconnecting the grasping portion (not shown) and bifurcated drive portion 3132. Clamp lever 3130 is pivotably connected to housing 110 via pivots 3134 that are disposed at a free end of bifurcated drive portion 3132 of clamp lever 3130, above a longitudinal axis of outer drive sleeve 210.

Linkages 3160 are disposed on either side of rigid slider 3256 and within bifurcated drive portion 3132, although linkages 3160 may alternatively be disposed outside of bifurcated drive portion 3132 or in any other suitable position. Further, in some aspects, only one linkage 3160 is provided. Linkages 3160 are pivotably coupled, towards distal end portions thereof, to bifurcated drive portion 3132 via pivots 3162. In aspects, pivots 3162 are disposed above the longitudinal axis of outer drive sleeve 210. Linkages 3160 are further pivotably coupled, towards proximal end portions thereof, to rigid slider 3256 via pivots 3164. Rigid slider 3256 may be longitudinally fixed but rotatably coupled to outer drive sleeve 210 to enable rotation, or may include an inner retainer fixedly engaged with outer drive sleeve 210 and an outer slider longitudinally fixed but rotatably coupled to the inner retainer to likewise enable rotation. Rigid slider 3256 may be similar to the configurations detailed above or may be provided in any other suitable manner.

As a result of the above-detailed configuration, actuation of clamp lever 3130 moves bifurcated drive portion 3132 proximally which, in turn, urges linkages 3160 proximally to thereby urge rigid slider 3256 proximally to translate outer drive sleeve 210 proximally to move clamp jaw 282 (FIG. 1) towards the clamping position and to apply the jaw force. Further, the above-detailed configuration illustrated in FIG. 12 provides for an increased mechanical advantage in that it enables positioning of the force transfer pivot axis, e.g., the pivot axis about which the distal end portion of linkage 3160 is connected to bifurcated drive portion 3132, closer to the pivot axis about which clamp lever 3130 is pivotably connected to housing 110. Thus, with the increased mechanical advantage, a relatively smaller lever force is required to achieve the same jaw force (and jaw pressure) or, put another way, the same lever force achieves a relatively greater jaw force (and jaw pressure). The location of the force transfer pivot axis may be selected to achieve a desired mechanical advantage and, thus, a desired resultant jaw force in response to an input lever force.

Figure 13:
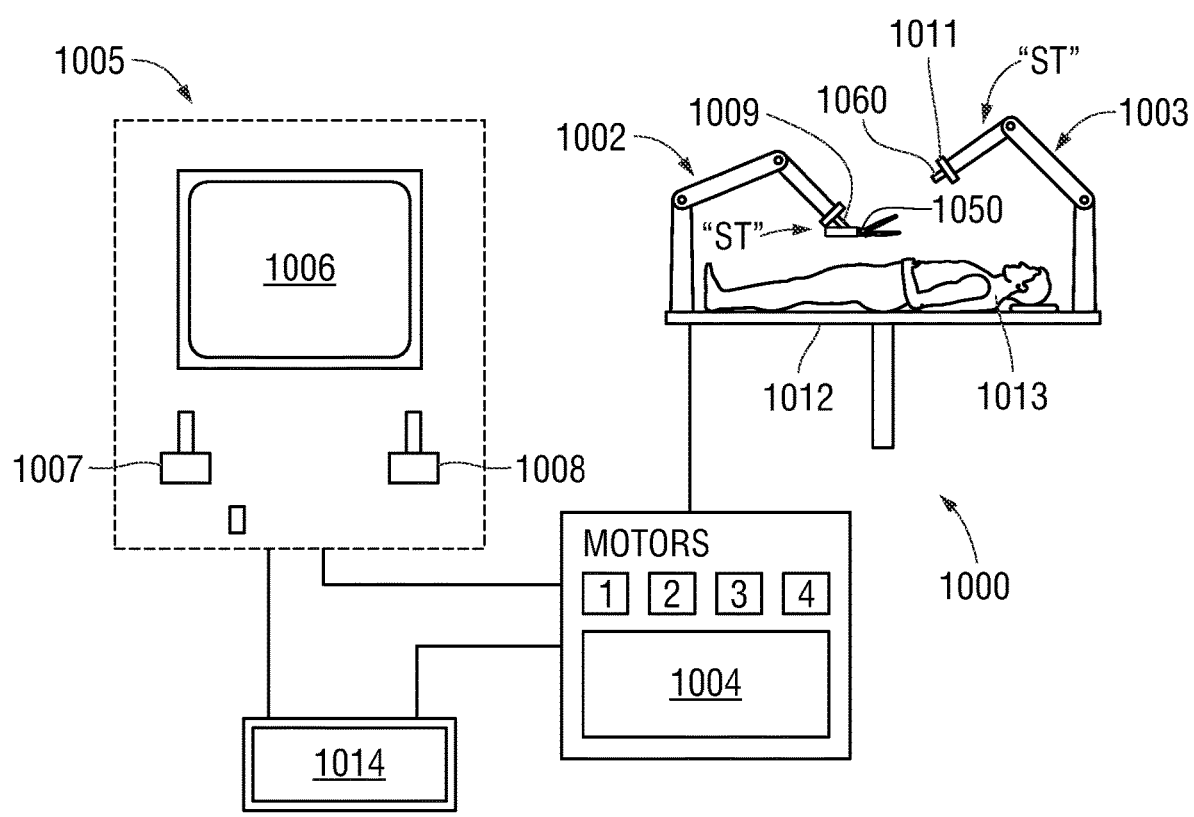
FIG. 13 is a schematic illustration of a robotic surgical system configured for use in accordance with the present disclosure.

Referring to FIG. 13, a robotic surgical system in accordance with the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector 1050, 1060. One of the surgical tools "ST" may be ultrasonic surgical instrument 10 (FIG. 1), wherein manual actuation features thereof, e.g., clamp lever 130 (FIG. 1), are replaced with robotic inputs. The other surgical tool "ST" may include any other suitable surgical instrument, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

With respect to robotic implementations, although the clamp lever is removed and replaced with a robotic input, the ultrasonic surgical instrument may still include a rigid slider configuration wherein the instrument is tuned to provide a jaw force (and jaw pressure) and a input force (in place of the lever force). The input force may be tuned to requirements of the robotic arm 1002 or in any other suitable manner. Further, due to the use of a rigid slider configuration without any dampening features, the robotic arm 1002 may be configured to sense the jaw force applied (based on a torque, displacement, and/or current of the driving motor) without the need for sensing equipment within the attachable ultrasonic surgical instrument. The determined jaw force may be displayed to the operator and/or utilized to provide corresponding tactile feedback to the operator at manual input device(s) 1007, 1008.

While several configurations of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

What is claimed is:

1. A surgical instrument, comprising:
a housing;
an end effector including a clamp jaw pivotable from an open position towards a clamping position;
a drive member extending distally from the housing, the drive member operably coupled to the clamp jaw such that translation of the drive member pivots the clamp jaw from the open position towards the clamping position; and
a clamp lever pivotably coupled to the housing and operably coupled to the drive member via at least one rigid component such that a force input by the clamp lever is substantially equal to a force output to the drive member, wherein the at least one rigid component includes a rigid slider configured to translate longitudinally, and wherein actuation of the clamp lever translates the rigid slider proximally to thereby move the drive member proximally to pivot the clamp jaw towards the clamping position, and
wherein the clamp jaw is configured to provide a jaw force to tissue clamped between the clamp jaw and an opposing structure, measured at about 0.192 inches from a distal end of the clamp jaw, of from about 1 lbf to about 8 lbf in response to a full actuation of the clamp lever.

2. The surgical instrument according to claim 1, wherein a lever force, measured at a midpoint of the clamp lever, of from about 1 lbf to about 10 lbf is required to fully actuate the clamp lever.

3. The surgical instrument according to claim 1, further comprising a waveguide extending distally from the housing and having a blade at a distal end thereof, the blade defining the opposing structure, the waveguide configured to transmit ultrasonic energy to the blade, wherein the clamp jaw is configured to oppose the blade in the clamping position thereof.

4. The surgical instrument according to claim 3, further comprising an ultrasonic transducer mounted on the housing, the ultrasonic transducer coupled to the waveguide and configured to generate ultrasonic energy for transmission along the waveguide to the blade.

5. The surgical instrument according to claim 1, wherein the clamp lever is pivotably coupled to the housing on a first side of a longitudinal axis of the drive member, wherein the clamp lever is actuatable via a grasping portion disposed on a second, opposite side of the longitudinal axis, and wherein the rigid slider is substantially aligned on the longitudinal axis.

6. The surgical instrument according to claim 1, wherein the clamp lever includes a proximal contact surface configured to urge the rigid slider proximally in response to actuation of the clamp lever.

7. The surgical instrument according to claim 1, wherein the at least one rigid component further includes a linkage coupled between the rigid slider and the clamp lever, wherein actuation of the clamp lever urges the linkage proximally to thereby urge the rigid slider proximally.

8. The surgical instrument according to claim 1, wherein the full actuation of the clamp lever includes moving the clamp lever from an initial position to a hard stop.

9. The surgical instrument according to claim 8, wherein the hard stop is defined by contact of a portion of the clamp lever with a portion of the housing.

10. A surgical instrument, comprising:
a housing;
a waveguide extending distally from the housing and having a blade at a distal end thereof;
a drive member and a support member, both the drive member and the support member extending distally from the housing;
a clamp jaw pivotably supported at a distal end portion of the support member and operably coupled to a distal end portion of the drive member such that translation of the drive member relative to the support member pivots the clamp jaw relative to the blade from an open position towards a clamping position, the clamp jaw including a tissue-contacting surface configured to oppose the blade in the clamping position of the clamp jaw, the tissue-contacting surface defining a tissue-contacting surface area;
a clamp lever pivotably coupled to the housing;
a drive assembly operably coupling the clamp lever with the drive member such that a force input by the clamp lever is substantially equal to a force output to the drive member, the drive assembly including a rigid slider configured to translate longitudinally, wherein actuation of the clamp lever translates the rigid slider proximally to thereby move the drive member proximally to pivot the clamp jaw towards the clamping position, and
wherein the clamp jaw, in response to a full actuation of the clamp lever, imparts an average jaw pressure of from about 35 psi to about 285 psi to tissue clamped between the tissue-contacting surface of the clamp jaw and the blade.

11. The surgical instrument according to claim 10, wherein a lever force, measured at a midpoint of the clamp lever, of from about 1 lbf to about 10 lbf is required to fully actuate the clamp lever.

12. The surgical instrument according to claim 10, further comprising an ultrasonic transducer mounted on the housing, the ultrasonic transducer coupled to the waveguide and configured to generate ultrasonic energy for transmission along the waveguide to the blade.

13. The surgical instrument according to claim 10, wherein the clamp lever is pivotably coupled to the housing on a first side of a longitudinal axis of the drive member, wherein the clamp lever is actuatable via a grasping portion disposed on a second, opposite side of the longitudinal axis, and wherein the rigid slider of the drive assembly is substantially aligned on the longitudinal axis.

14. The surgical instrument according to claim 10, wherein the clamp lever includes a proximal contact surface configured to urge the rigid slider proximally in response to actuation of the clamp lever.

15. The surgical instrument according to claim 10, wherein the drive assembly further includes a linkage coupled between the rigid slider and the clamp lever, wherein actuation of the clamp lever urges the linkage proximally to thereby urge the rigid slider proximally.

16. The surgical instrument according to claim 10, wherein the full actuation of the clamp lever includes moving the clamp lever from an initial position to a hard stop.

17. The surgical instrument according to claim 16, wherein the hard stop is defined by contact of a portion of the clamp lever with a portion of the housing.

18. The surgical instrument according to claim 10, wherein the clamp lever is pivotably coupled to the housing on a first side of a longitudinal axis of the drive member, wherein the clamp lever is actuatable via a grasping portion disposed on the first side of the longitudinal axis, and wherein a rigid slider of the drive assembly is substantially aligned on the longitudinal axis.

\* \* \* \* \*